(12) United States Patent
Mayer et al.

(10) Patent No.: US 11,382,780 B2
(45) Date of Patent: Jul. 12, 2022

(54) SYSTEM AND METHOD FOR LOADING A SELF-EXPANDABLE PROSTHESIS ON A DELIVERY DEVICE

(71) Applicant: BIOTRONIK AG, Buelach (CH)

(72) Inventors: Maximilian Mayer, Ebersberg (DE); Christian Erbe, Dachau (DE); Markus Hepke, Waltrop (DE)

(73) Assignee: BIOTRONIK AG, Buelach (CH)

(*) Notice: Subject to any disclaimer, the term of this patent is extended or adjusted under 35 U.S.C. 154(b) by 0 days.

(21) Appl. No.: 16/972,946

(22) PCT Filed: Jun. 20, 2019

(86) PCT No.: PCT/EP2019/066380
§ 371 (c)(1),
(2) Date: Dec. 7, 2020

(87) PCT Pub. No.: WO2019/243522
PCT Pub. Date: Dec. 26, 2019

(65) Prior Publication Data
US 2021/0244555 A1 Aug. 12, 2021

(30) Foreign Application Priority Data
Jun. 22, 2018 (EP) .................................. 18179248

(51) Int. Cl.
*A61F 2/95* (2013.01)
*A61F 2/24* (2006.01)

(52) U.S. Cl.
CPC .... *A61F 2/9522* (2020.05); *A61F 2210/0014* (2013.01); *A61F 2240/001* (2013.01)

(58) Field of Classification Search
CPC ........ A61F 2/9522; A61F 2/95; A61F 2/2412; A61F 2240/001; A61F 2210/0014
See application file for complete search history.

(56) References Cited

U.S. PATENT DOCUMENTS

| | | | | |
|---|---|---|---|---|
| 10,188,515 | B2* | 1/2019 | Duffy | A61F 2/243 |
| 2007/0239271 | A1* | 10/2007 | Nguyen | A61F 2/9525 |
| | | | | 623/2.11 |
| 2014/0331475 | A1* | 11/2014 | Duffy | A61F 2/9525 |
| | | | | 29/446 |

FOREIGN PATENT DOCUMENTS

| | | | |
|---|---|---|---|
| WO | 2013045262 A1 | 4/2013 | |
| WO | WO-2013045262 A1 * | 4/2013 | ........... A61F 2/2436 |

OTHER PUBLICATIONS

International Search Report from the corresponding International Patent Application No. PCT/EP2019/066380, dated Sep. 3, 2019.

* cited by examiner

*Primary Examiner* — Bayan Salone
(74) *Attorney, Agent, or Firm* — Greer, Burns & Crain, Ltd.; Steven P. Fallon

(57) ABSTRACT

A system and method for loading a self-expandable prosthetic device into a delivery device. The system includes a compression member that has a chamber with a tapered inner surface, a support member, a splay member and a constriction member. The compression member and the constriction member can be releasably attached to each other directly or via a spacer element, in two different positions relative to each other. The first position offers an optimal configuration for releasable attachment of the prosthetic device to the delivery device and the second position offers an optimal configuration for reducing the diameter of the delivery device. The risk of damaging the delivery device and to the prosthetic device during the loading procedure is thereby reduced.

16 Claims, 20 Drawing Sheets

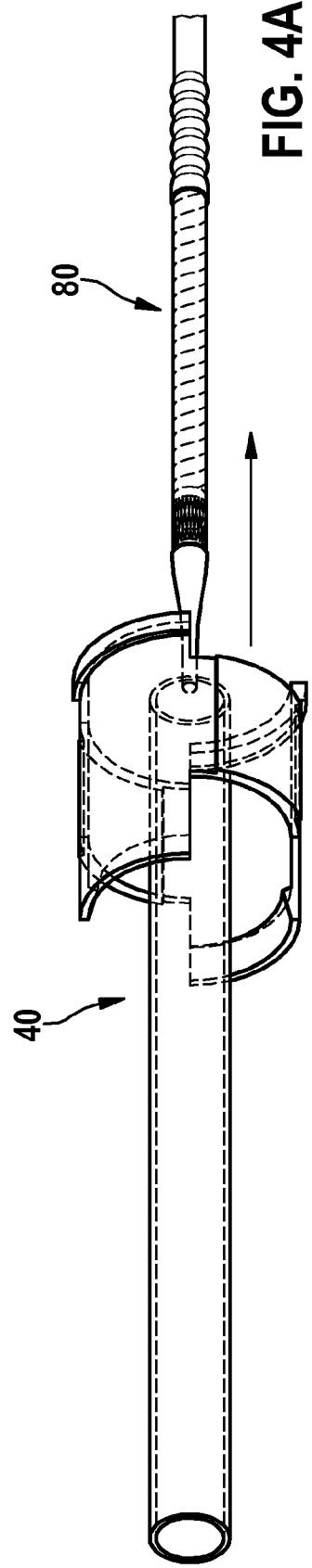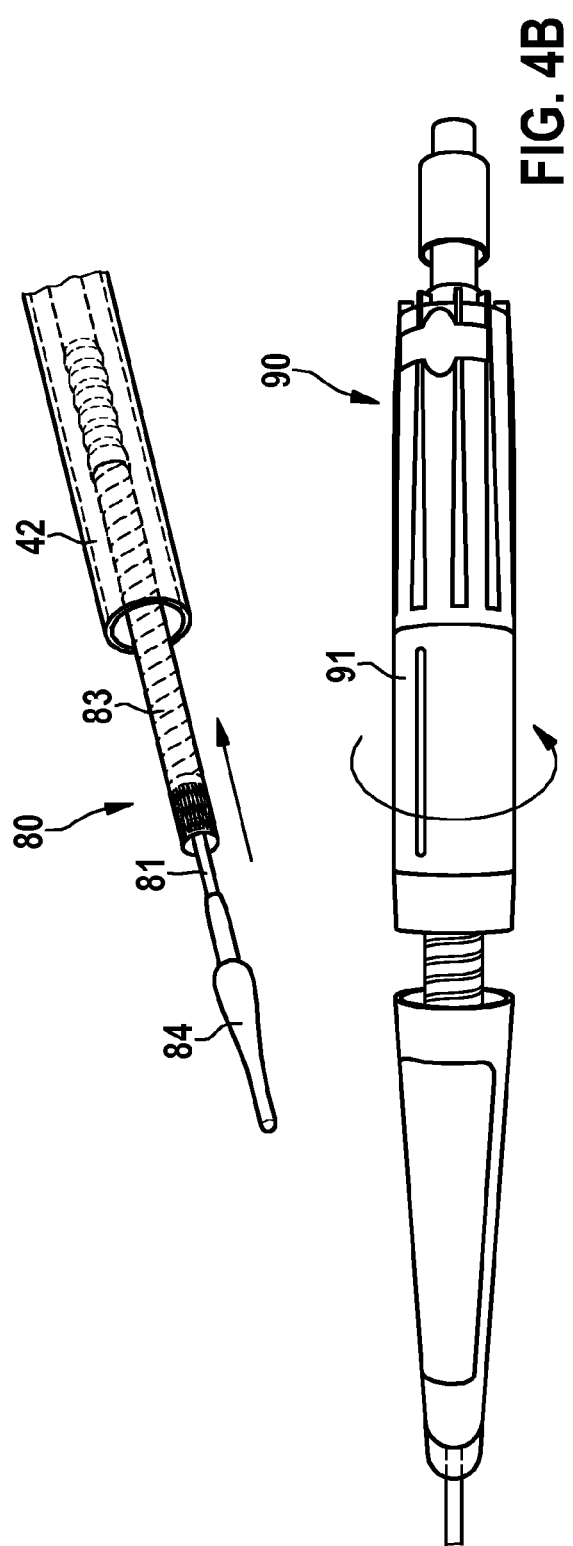

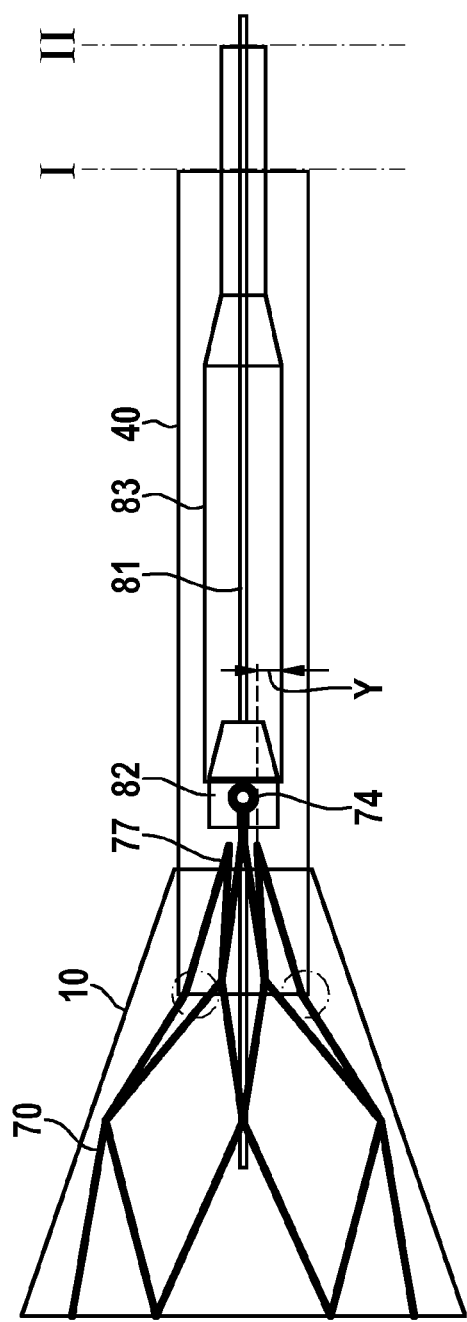

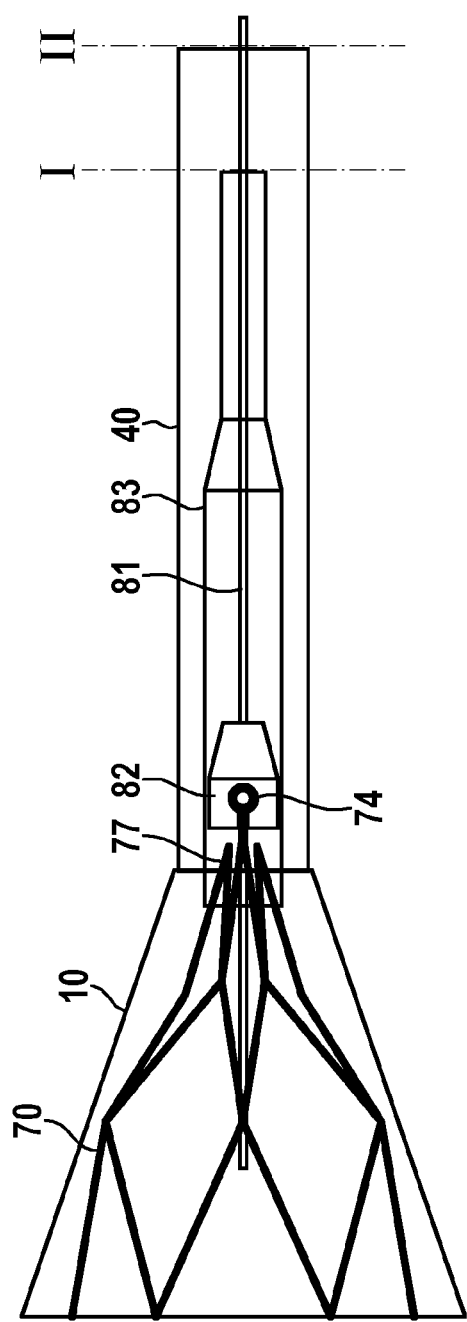

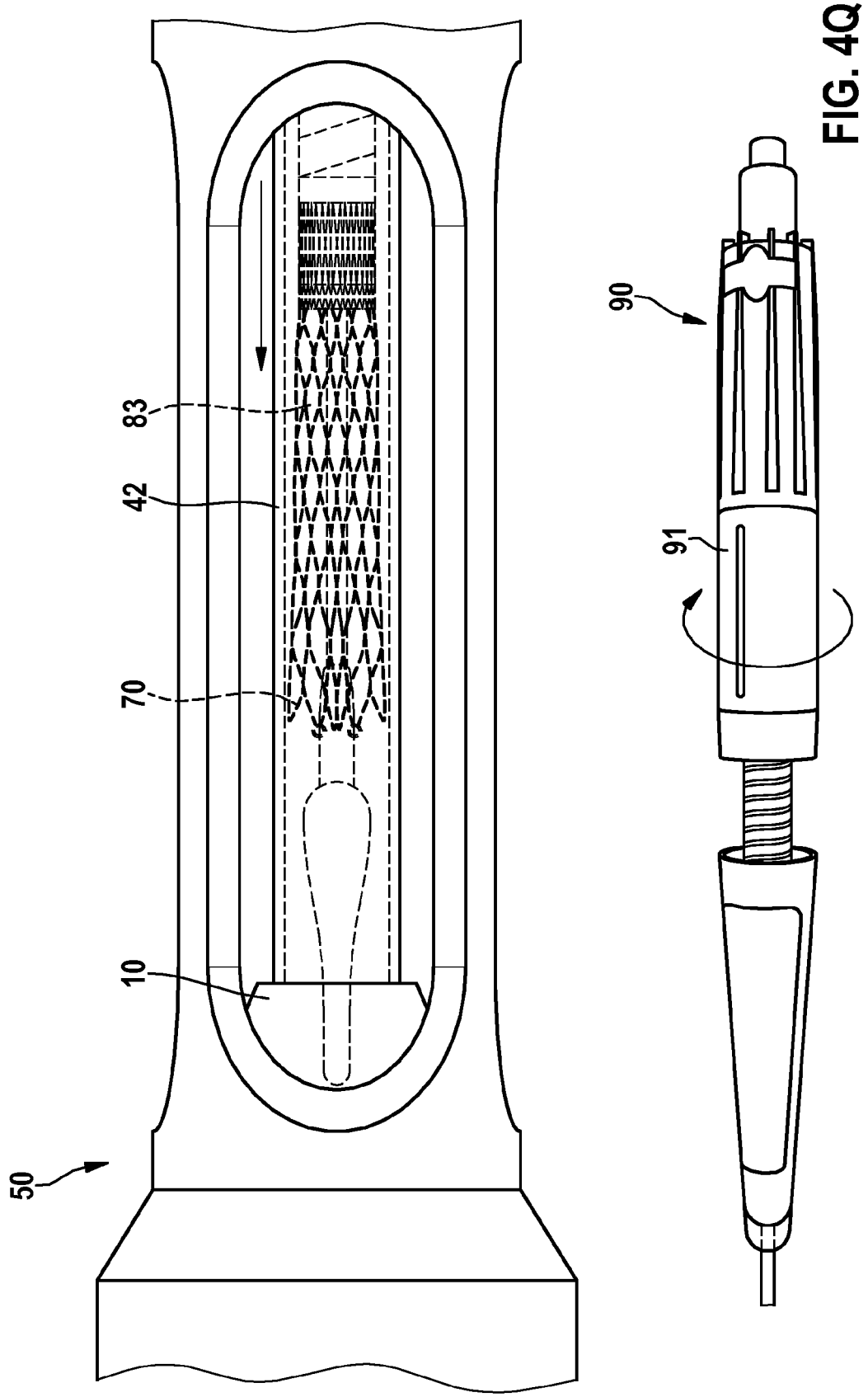

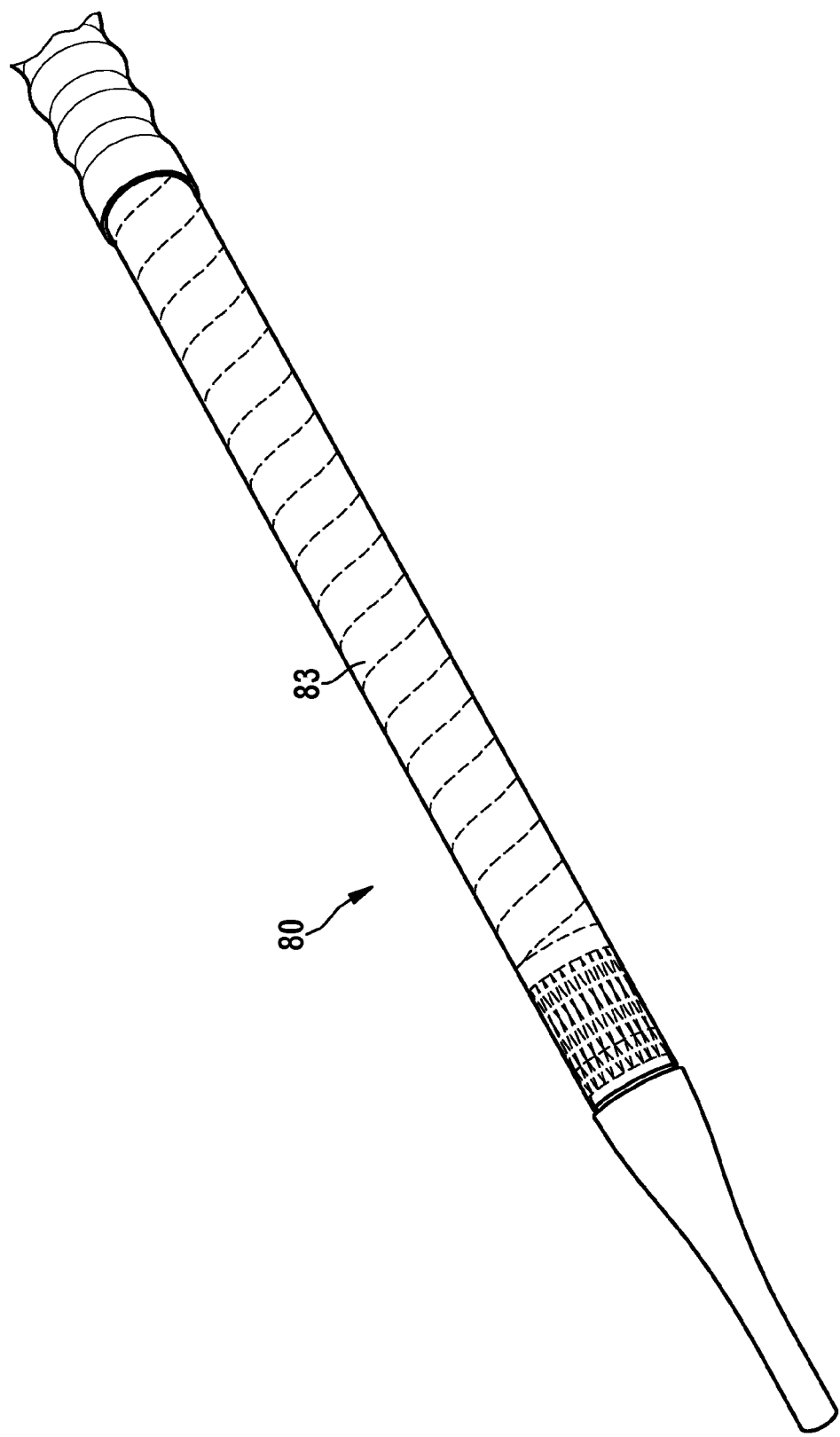

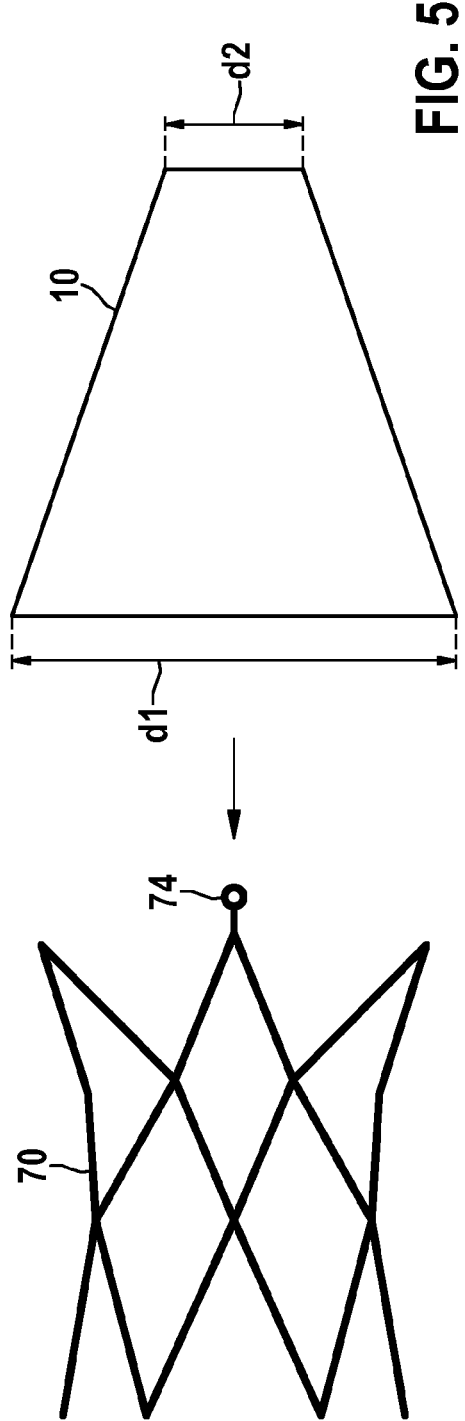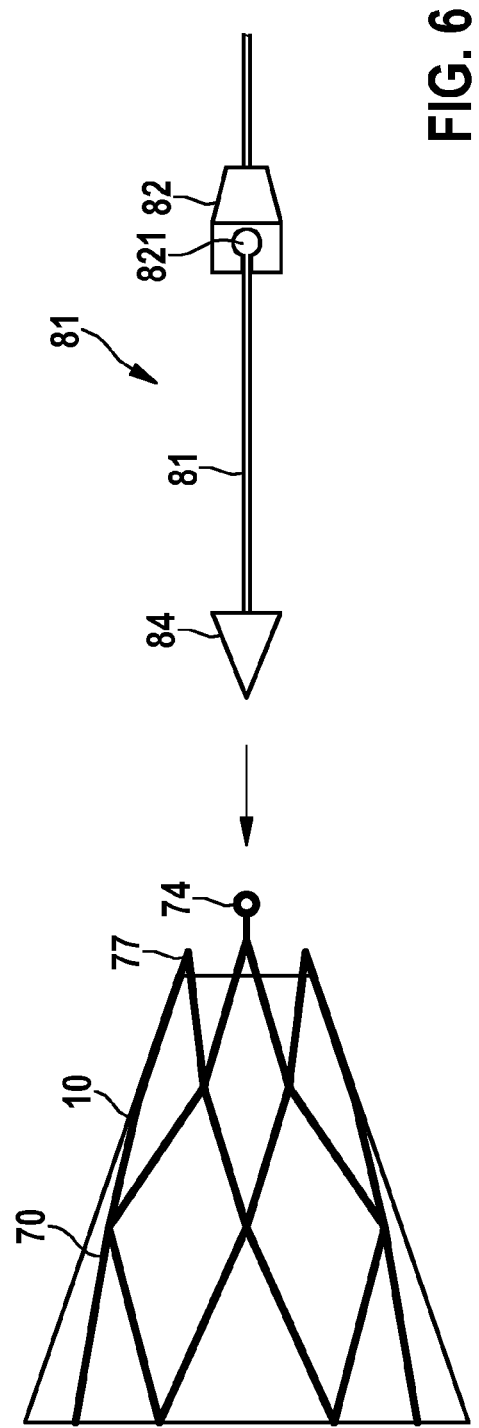

SYSTEM AND METHOD FOR LOADING A SELF-EXPANDABLE PROSTHESIS ON A DELIVERY DEVICE

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/066380, which was filed Jun. 20, 2019, which application claimed priority from European Application EP18179248.2, which was filed Jun. 22, 2018.

FIELD OF THE INVENTION

The invention relates to a system and method for loading a self-expandable prosthetic device into a delivery device.

BACKGROUND

Self-expandable prosthetic devices such as stents or artificial heart valves attached to a stent have to be loaded into a delivery device in order to be delivered to the position in the body where they are to serve their function.

US 2007/0239271 A1 describes a system for loading a replacement valve prosthesis onto a minimally invasive delivery system, such as a delivery catheter. The system may include one or more frustoconical housings which define a tapered surface. The prosthesis of US 2007/0239271 A1 may be moved along the tapered surface to compress the prosthesis. Methods of loading the replacement valve prosthesis are also described therein.

Several systems for loading such prosthetic devices into delivery devices as well as methods for doing so are known in the art. However, there is a need in the art for a better system and a method that allows loading of self-expandable devices by a single person with reduced risk of damaging the prosthetic device during loading.

SUMMARY OF THE INVENTION

In a first aspect of the invention, a loading system for loading a self-expanding prosthetic device into a delivery device, is provided. The loading system includes:

a compression member including a chamber with a tapered inner surface extending along a longitudinal axis from a first distal end having a first diameter to a second proximal end having a second diameter that is smaller than the first diameter;

a support member configured to be releasably attached to the first distal end of the compression member;

a splay member;

a constriction member, wherein the second proximal end of the compression member has an opening that is sized to slidably receive a first distal end of the constriction member; wherein the compression member and the constriction member are configured to be releasably attachable to each other directly or through a spacer element; and releasable attachment structures between the compression member and the constriction member configured to provide a first and a second attachment position of the compression member and the constriction member relative to each other; wherein the first and the second attachment positions are offset relative to each other along the longitudinal axis of the loading system.

The method preferably uses the preferred loading system and includes the steps of:

providing a delivery device including a shaft with a distal end, a retaining element attached to the shaft, a compartment adapted to receive the prosthetic device defined between a distal end of the shaft and the retaining element, and a distal sheath movable between a closed position fully covering the compartment and an open position uncovering the compartment, the prosthetic device including a stent and at least two retainers at its distal end and having an expanded and a collapsed condition;

engaging the constriction member with the distal end of the delivery device;

moving the distal sheath of the delivery device proximally to expose the retaining element;

placing the proximal end of the prosthetic device on the support member and the compression member on the support member to enclose the prosthetic device within the tapered chamber of the compression member and thereby compressing the distal end of the prosthetic device;

pushing the retainers of the prosthetic device contained in the compression member apart in the radial direction with a hollow member of the splay member;

inserting the distal end of the shaft of the delivery device through the second opening of the compression chamber and through the lumen of the prosthetic device to align the retainers of the prosthetic device and the retaining element of the delivery device;

withdrawing the hollow member in the distal direction so that the retainers of the prosthetic device engage with the retaining element of the delivery device;

sliding the constriction member distally into the first attachment position;

sliding the distal sheath of the delivery device distally to cover the retaining element;

sliding the constriction member proximally into the second attachment position;

pulling the prosthetic device into the constriction member;

closing the compartment of the delivery device by sliding the distal sheath distally into the closed position.

It will be clear to the skilled person that all the steps do not have to be performed exactly in this order. The order of some of the steps can be switched.

BRIEF DESCRIPTION OF THE DRAWINGS

The present invention may best be understood from the following detailed description and figures. The invention is however not restricted to the embodiments detailed in this section.

FIG. 5 schematically shows a prosthetic device and a compression member and shows how they are to interact;

FIG. 6 schematically shows a prosthetic device inside a compression chamber and a distal end of a delivery device.

DETAILED DESCRIPTION OF THE PREFERRED EMBODIMENTS

Figure 1:
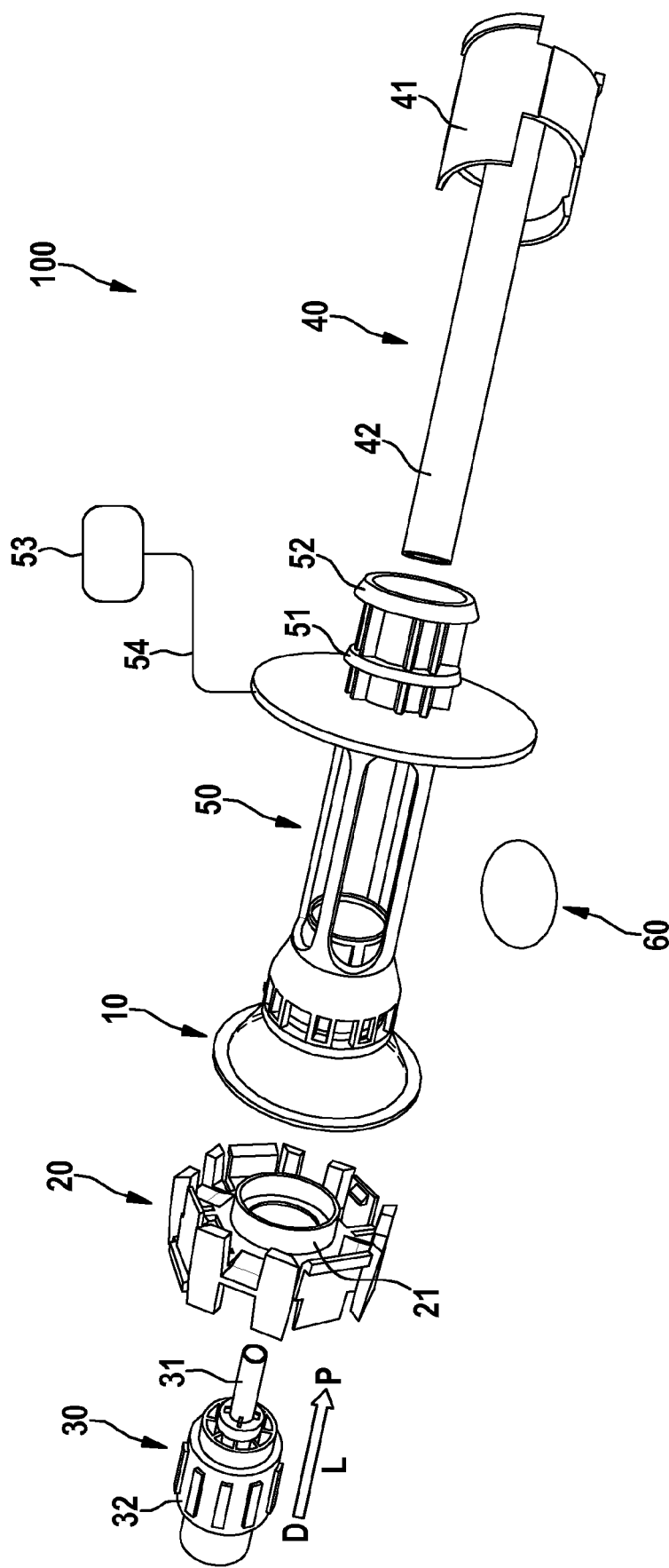
FIG. 1 is an illustration in exploded view of the loading system according to the invention.

One advantage of a preferred loading system of the invention is that the compression member and the constriction member can be attached to each other, either directly or through the intermediary of a spacer element, in two different positions relative to each other. This is in contrast to earlier systems in which only a single fixed position of the two elements relative to each other was possible. This is advantageous because the inventors have found that different relative positions of the two elements at the different stages of a loading procedure provide optimal handling with reduced risk of damage to the prosthetic device.

The self-expanding prosthetic device and the delivery device into which it is to be loaded can also be part of the loading system.

Advantageously, in the first attachment position between the compression member and the constriction member (either directly or through a spacer element), the distal end of the constriction member is positioned distally relative to the second end of the tapered inner surface of the compression member along the longitudinal axis L, and in the second attachment position, the distal end of the constriction member coincides with or is positioned proximally to the second end of the tapered inner surface of the constriction member along the longitudinal axis L. In the first attachment position, the loading system offers an optimal configuration for releasable attachment of the prosthetic device to the delivery system. This is due to the fact that the distal end of the constriction member extends into the tapered chamber of the compression member and thereby further decreases the diameter of the distal end of the prosthetic device when this device is positioned inside and locked into the compression member by the support member. This ensures that the distal end of the sheath of the delivery device can be safely slid over the retaining member of the delivery device and the retainers of the prosthetic device without causing any damage to the prosthetic device or the distal end of the sheath. In the second attachment position, the constriction member does not extend into the tapered chamber of the compression member. This configuration ensures that the prosthetic device is not exposed to the distal edge of the constriction member when it is pulled into the constriction member and therefore reduces the risk of damage to the prosthetic device when the prosthetic device is being pulled into the constriction member. The advantages of the two positions are further explained below with reference to the figures.

The first (distal) and second (proximal) opening of the compression member are openings that respectively coincide or are connected, preferably along the longitudinal axis L, to the first (distal) and second (proximal) opening of the chamber of the compression member. The longitudinal axis L in the context of this disclosure is the axis that extends through the centre of the loading device, the prosthetic device and the delivery device. The terms distal and proximal apply to the different elements as follows. The distal side or end when referring to the loading system is the side or end that faces towards the splay element along the longitudinal axis L. The proximal side or end in contrast faces towards the constriction element along the longitudinal axis L. The distal side or end when referring to the prosthetic device by convention refers to the side or end of the prosthetic device that faces away from the heart in the implanted state. Conversely, the proximal side or end of the prosthetic device is the side or end that faces towards the heart in the implanted state. For example when the prosthetic device is an aortic heart valve, the proximal end of the device corresponds to the inflow of the heart valve device which is located on the side of the ventricle in the implanted state whereas the distal end is the outflow which in the implanted state is located in the ascending aorta. When referring to the delivery device, the distal end is the end into which the prosthetic device is loaded and the proximal end is the end that optionally includes a handle that can be actuated by the operator. It should be noted that the distal to proximal axis direction of the different elements (loading device, prosthetic device and delivery device) can point in opposite directions depending on the convention applied. In the context of this disclosure, when referring to a movement of an element in a distal or proximal direction along the axis L, the movement usually refers to the axis L as defined for the loading device, unless stated otherwise.

The chamber of the compression member is sized and shaped to be adapted to receive a distal end of the prosthetic device that is to be loaded into the delivery device. The support member is adapted to be releasably attachable to the compression member in such a way that the prosthetic device can be trapped inside the chamber of the compression member. In this state, the distal end of the prosthetic device is radially constricted due to the tapered inner surface of the compression member.

The support member includes a through bore that is sized to slidably receive at least a hollow (cylindrical) member of the splay member (see further details below). Preferably, a radially external surface of the support member is round. This regular outer shape allows the user to easily rotate the support member, along with the compression member and the prosthetic device relative to the delivery device for easy alignment of the retainers of the prosthetic device to the retaining element of the delivery device.

In one embodiment, the support member includes a receptacle in the shape of an annular collar configured to receive a (proximal) end of the prosthesis device. The collar is preferably located on the proximal side of the support member and is preferably also centred on the longitudinal axis L to provide an easy way for positioning the prosthetic device onto the support member. In an even more advantageous embodiment, the support member includes a receptacle in the shape of an annular collar configured to receive a (proximal) end of a prosthetic device on each of its two opposing sides that extend radially from the longitudinal axis L. In this embodiment, the collars on each of the opposing sides are configured to receive a (proximal) end of a prosthetic device of different sizes. That is to say, the collars on the two opposing sides of the support members are of different sizes (they have different diameters). This allows a same loading system to be used to load prosthetic devices of different sizes onto a delivery device.

In one embodiment, the support member includes at least one vent hole, and preferably several vent holes. The one or several vent holes are configured in such a way that air, which is trapped between the support member and the constriction member when the two members are releasably attached to each other, is able to escape the chamber formed between the two members through the at least one vent hole. This is particularly useful when part of the procedure is performed while the loading device and the distal end of the delivery device are submerged in a liquid solution (see below). The one or several vent holes allow ensuring that no air bubbles are trapped inside the delivery device once the prosthetic device is loaded onto the delivery device.

In one embodiment, the compression member is at least partially made of a transparent material to be adapted for visual monitoring of the prosthetic device during the loading procedure. Such monitoring allows ensuring greater control over the loading procedure and therefore reducing the risk of damage to the prosthetic device.

In one embodiment, the loading system includes a spacer element. The spacer element preferably has an elongated shape with a through bore that extends along the longitudinal axis L. It preferably extends proximally along the longitudinal axis L relative to the compression member and includes an opening proximally to the second (proximal) opening of the compression member that is configured to slidably receive the constriction element. The opening in the spacer element is preferably aligned on the longitudinal axis L with the second (proximal) opening of the compression member and with the centre of the through bore of the support member when the support member is releasably attached to the compression member. The advantage of this aligned configuration is that the constriction member is aligned on the longitudinal axis L when it interacts with the compression member and the spacer element and thereby allows preventing damage that could otherwise be caused to the prosthetic device through bending during the loading procedure.

The spacer element is preferably at least partially made of a transparent material or includes at least one opening adapted for visual monitoring of the loading procedure, and more specifically, of the alignment of the retainers of the prosthetic device with the retaining member of the delivery device. Specifically, it allows monitoring the alignment of the retainers with the recesses on the retaining member. The spacer element is preferably rotatable around the longitudinal axis L relative to the compression member (and therefore also relative to the support member and the prosthetic device contained between the compression member and the support member). This embodiment is particularly advantageous when the spacer element includes at least one opening adapted for visual monitoring of the loading procedure. In this way, the spacer element can be rotated to offer a better visibility to the operator of the attachment of the prosthetic device to the delivery system. This allows improving the speed and accuracy of the alignment of the retainers and retaining element.

In one embodiment, the spacer element includes a flat surface on at least part of its radial outer contour. The flat surface of the outer contour of the spacer element is arranged in such a way that when the loading system rests on a flat surface, such as a table, the flat surface on which it rests and the flat surface of the spacer element interact with each other. This arrangement prevents the loading system from rolling off the flat surface and provides a system that is easier to handle because the loading system cannot inadvertently role away when put down for example on an operating table. Preferably at least part of the radial outer contour of the spacer element has multiple flat surfaces. Most preferably, at least part of the radial outer contour of the spacer element has the shape of a hexagon or an octagon. Such an arrangement provides further flat surfaces on the spacer element, which further improves handling.

In one embodiment, the splay member includes a hollow member. This hollow member preferably includes a (essentially) cylindrical portion. The hollow member has an outer diameter sized to interact with an inner surface of the (distal portion of the) prosthetic device when the prosthetic device is located inside the tapered chamber of the compression member to reversibly push the at least two retainers located at (or towards) the distal end of the prosthetic device away from each other in a radial direction. The inner diameter of the hollow member of the splay member is configured to slidably receive the distal end of the delivery device into which the prosthetic device is to be loaded.

The splay member and the support member of the loading system are preferably adapted to be attached to each other through a releasable attachment structures. At least one of the releasable attachment structures is preferably a snap lock or a form fit frictional attachment structures.

In one embodiment, the splay member, in addition to the hollow member, includes a retainer member as well as a biasing element (preferably a spring) that is located between the retainer member and the hollow cylindrical member, wherein the retainer member includes a surface that is adapted to rest on the distal side of the loading base and the biasing element is placed to bias the hollow member distally along the longitudinal axis L relative to the retainer member. This arrangement allows for better control of the splaying process since the hollow member of the splay member does not have to be pulled back in the distal direction by the operator manually when the retainers and retaining members are aligned with each other but is automatically pushed back when the pressure applied onto the retainer member of the splay member by the operator is released. Then the pressure is released, the retainers of the prosthetic device therefore automatically move towards each other in the radial direction to interact with the retaining element of the delivery device. It should be noted that the hollow member could have different shapes, as long as it is adapted to push the retainers of the prosthetic device apart from each other when the prosthetic device is retained in the compression member by the support member.

In one embodiment, the loading system further includes a reflecting member (such as a mirror) that is placed to allow monitoring of the loading of the prosthetic device into the delivery device from a position that would not otherwise be visible to the operator performing the loading procedure. This additional element therefore allows the operator to perform the loading procedure more efficiently.

In one embodiment, the constriction member is at least partially made of a transparent material to allow monitoring of the loading procedure by the operator. More specifically, when at least a distal portion of the constriction member is made of a transparent material, the operator can monitor that the prosthetic device is not being damaged while being pulled into the constriction member during the loading procedure.

In one embodiment, the loading system further includes a stopper element. The stopper element is preferably attached to the compression member or the spacer element and includes a flexible portion such as a wire. The length of the flexible portion of the stopper element is such that when a portion of the stopper element, such as an end of the flexible portion or optionally a handle, is held against the outer sheath of the delivery device when the distal end of the delivery device is inserted into the loading device, either directly at the proximal end of the constriction member or at a predefined position (such as a mark) on the outer sheath of the delivery device, the flexible portion of the stopper element is stretched to its maximum capacity when the position at which the prosthetic device has been sufficiently pulled into the constriction member has been reached. The stopper element is therefore designed in such a way that it indicates to the operator at which point the prosthetic device has been sufficiently pulled into the constriction member so that the distal end of the sheath of the delivery device can be slid over the prosthetic device without causing damage to either of the distal end of the sheath or the prosthetic device. As a result, the stopper element provides a simplified loading procedure, since the operator does not have to visually inspect the loading device itself at this stage of the procedure.

In one embodiment, the constriction member has a lumen with an inner diameter that is configured to receive the prosthetic device in a compressed state. The compressed state is a state of the prosthetic device in which its diameter is reduced in such a way that the distal end of the sheath of the delivery device can be slid over the prosthetic device without causing damage to either of the distal end of the sheath and the prosthetic device.

The delivery device in the context of this disclosure is a device that includes a shaft with a distal end, a retaining element attached to the shaft (or forming integral part of the shaft), a compartment adapted to receive the prosthetic device defined between a distal end of the shaft and the retaining element, and a distal sheath movable between a closed position fully covering the compartment and an open position uncovering the compartment. The delivery device preferably also includes a handle to which the shaft and the sheath are attached. The sheath is preferably configured to be movable axially relative to the shaft and the handle by an actuating element on the handle.

The retaining element is preferably configured as an element with recesses adapted to receive the retainers of the prosthetic device. The interaction between the retaining element (or more specifically the recesses) and the retainers provide releasable attachment structures of the prosthetic device to the delivery device. This releasable attachment is made independent of the presence of the loading system (or at least of the compression member, the constriction member and the support base) by distally moving the distal end of the sheath of the delivery system over the retaining element and the retainers. The interaction between the retaining element, the retainers and the sheath of the delivery device therefore provides releasable attachment structures between the prosthetic device and the delivery device.

The handle of the delivery device preferably includes a marking that indicates a position of the actuating element relative to the handle in which the distal end of the sheath covers the retaining element of the shaft. The marking therefore indicates when the prosthetic device is releasably attached to the delivery device. An advantage of such an arrangement is that the operator does not need to observe the advancement of the distal end of the shaft in order to know when the releasable attachment state is reached. This can indeed be difficult when having at the same time to actuate the actuating element of the handle.

The prosthetic device is preferably self-expandable. It preferably includes a stent made of a self-expandable material such as nitinol. The prosthetic device includes at least two (preferably 3) retainers at or near its distal end. The retainers of the device are configured to fit into the recesses of the retaining element of the delivery device in such a way that when they are covered by the sheath of the delivery device, the prosthetic device is releasably attached to the delivery device. For certain prosthetic device designs it may be necessary for distal ends that do not include a retainer to also be covered by the sheath of the delivery device in order for the prosthetic device to be releasably attached to the delivery device. The retainers can for example have the shape of eyelets that fit into the recesses of the retaining member of the delivery device.

The prosthetic device preferably has an expanded and a collapsed condition. The prosthetic device is preferably a stented artificial heart valve. Loading a stented artificial heart valve into a delivery device represents a particular challenge compared to loading of a bare stent. Such a prosthetic device is indeed more prone to being damaged during loading due to the presence of the functional element (the heart valve itself), which is usually made of a tissue such as pericardium. This functional element is normally attached to the stent by knots. The loading system of the present disclosure is particularly well suited for loading of stented artificial heart valves since it offers a more gentle way of loading the heart valve into the delivery device due to its two different attachment positions between the constriction member and the compression member (directly or via a spacer member).

The invention is also concerned with a method for loading a self-expandable prosthetic device into a delivery device, the delivery device including a shaft with a distal end, a retaining element attached to the shaft, a compartment adapted to receive the prosthetic device defined between the distal end of the shaft and the retaining element, and a distal sheath movable between a closed position fully covering the compartment and an open position uncovering the compartment, the prosthetic device including a stent and at least two retainers at or near its distal end and having an expanded and a collapsed condition.

In one embodiment, the step of pulling the prosthetic device into the lumen of the constriction member is performed by pulling the delivery system in the proximal direction along the longitudinal axis L. Since at this stage of the method, the prosthetic device is releasably attached to the prosthetic device, pulling the delivery device into the proximal direction along the longitudinal axis L will have the effect of also pulling the prosthetic device from the chamber of the compression member into the lumen of the constriction member. In a preferred embodiment, the loading system is configured in such a way that pulling the prosthetic device proximally in this step also slides the constriction member proximally from the first attachment position to the second attachment position. This has the advantage of avoiding damaging the prosthesis even if the step of transferring the system from one position to the other has been omitted by the operator.

In one embodiment, the part of the loading system that includes the prosthetic device is placed at a temperature of between 0° C. and 15° C., preferably 2° C. to 8° C. at least during the step of pulling the prosthetic device into the constriction member. This can for example be done by submerging the relevant part of the loading system in a saline solution that has the desired temperature. The advantage of performing this step at a low temperature is that the elasticity of the stent of the prosthetic device is reduced, especially if the stent is made of shape memory material such as nitinol. This reduces the risk of damage to the prosthetic device while performing the step of reducing the diameter of the prosthetic device to fit into the constriction member.

In one embodiment, at least the steps of inserting the distal end of the shaft to the step of closing the compartment are performed while at least the prosthetic device and the distal end of the delivery device are submerged in a liquid solution, preferably in a saline solution. The advantage of performing these steps under such conditions is that air bubbles cannot be enclosed into the delivery device.

The step of sliding the distal sheath of the delivery device is meant to provide releasable attachment between the prosthetic device and the delivery device. Depending on the prosthetic device and delivery device design, the distal end of the sheath of the delivery device may have to be slid also over additional distal ends of the prosthetic device that do not include retainers in order for the releasable attachment to be achieved.

In one embodiment, the step of sliding the distal sheath of the delivery device is performed by actuating (preferably by rotation) the actuator of the handle distally so that the distal end of the actuator coincides with a predefined marking on the handle which is indicative of the position at which the distal end of the sheath of the delivery device covers the retaining elements of the prosthetic device and in which therefore the prosthetic device is releasably attached to the delivery device. The operator thus does not need to visually inspect the releasable attachment position between the two devices while rotating the actuator of the handle, which makes the procedure easier to carry out.

In one embodiment, the step of pulling the prosthetic devices is performed after first collocating a part of the stopper element (such as a handle or an end of a flexible portion) with the delivery device either at the proximal end of the constriction member or at a redefined marking on the delivery device. The part of the stopper element that is collocated with a part of the delivery device is either attached to the predefined position on the delivery device by releasable attachment structures or held in position by the operator. The prosthetic device is then pulled into the constriction member by pulling the delivery device in the proximal direction relative to the loading device until the flexible portion of the stopper element is tensed. The stopper element is so designed that when the flexible portion of the stopper element is tensed, the prosthetic device has been pulled into the constriction member to a sufficient degree that the distal sheath of the delivery device can be slid over the prosthetic device without risking any damages to the delivery device or the prosthetic device. The advantage of performing this step in such a way is that the operator does not need to visually inspect whether the prosthesis has been pulled into the constriction member to a sufficient extent, which makes the loading procedure simpler.

All the embodiments disclosed in the context of the method also apply to the loading system. Similarly, the embodiments disclosed in the context of the loading system also apply to the method.

In view of all the foregoing, the below figure description and the figures, the skilled person readily understands that all the embodiments disclosed herein may also apply for loading a self-expandable prosthetic device into a delivery device for transapical delivery of said prosthetic device and to a respective method for doing the same. The skilled person is thereby aware which adaptations may need to be done in order to apply the system for loading and a respective method in transapical approaches.

FIG. 1 illustrates different components of the loading system 100 according to one embodiment. The loading system 100 includes a splay member 30, a support member 20, a compression member 10, a spacer element 50, a mirror 60, and a constriction member 40.

The splay member 30 includes a hollow member 31, a retainer member 32 and a biasing element (not shown). The hollow member 31 is biased in the distal direction relative to the retainer member 32 through the action of the biasing element. The support member 20 includes a collar 21 sized to receive a proximal end of the prosthetic device 70 that is to be loaded into a delivery device 80. The compression member 10 includes a chamber with a tapered inner surface that extends along the longitudinal axis L from a first distal end with a first diameter to a second proximal end with a second dimeter that is smaller than the first diameter (for more details regarding the diameters see FIG. 5). The compression member 10 and the support member 20 can be releasably attached to each other, in this case through a snap fit attachment structures. When attached to each other, the compression member 10 and the support member 20 form a chamber which is able to enclose a prosthetic device 70 that is to be loaded into the delivery device 80. A spacer element 50 is attached on the proximal side of the compression member 10 and includes attachment structures 51, 52 as well as a stopper element with a flexible element 54 (such as a wire) and a handle 53. The loading system 100 further includes a constriction member 40, which includes a tubular constriction region 42 and attachment structures 41. The attachment structures 41, 51 and 52 cooperate to provide two different attachment positions of the constriction member 40 relative to the spacer element 50 (and therefore also relative to the compression member 10). The mirror 60 is positioned to enable the operator to observe the loading procedure from an angle that would normally not be visible without rotating the loading system 100. FIG. 1 also defines the axis L that extends from a distal end D to a proximal end P.

Figure 2:
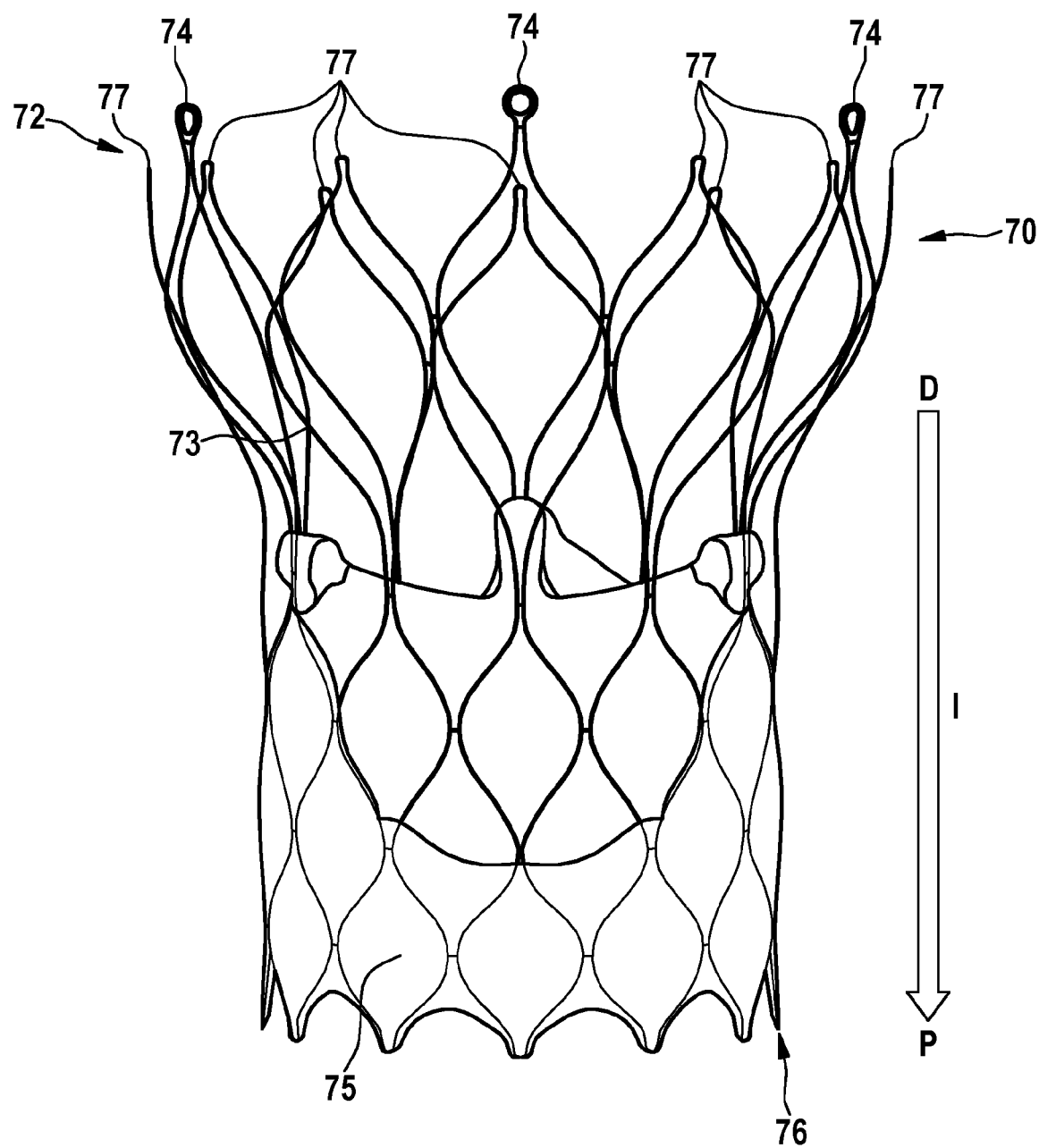
FIG. 2 is an illustration of a prosthetic device that can be loaded into a delivery device with the loading system of the invention.

FIG. 2 illustrates a prosthetic device 70 that can be loaded into a delivery device 80 through a loading system 100. The prosthetic device 70 is an artificial stented heart valve. It includes a stent 73 and a functional element 75. The stent includes a distal end 72 and a proximal end 76. Some of the distal ends 77 of the stent include retainers 74, which in this case are eyelets. FIG. 2 also indicates the longitudinal axis 1. It should be noted that at least in this case, the longitudinal axis 1 is aligned with the longitudinal axis L of FIGS. 1 and 3 but points in the opposite direction from a distal to a proximal end. This is due to different annotation conventions.

Figure 3:
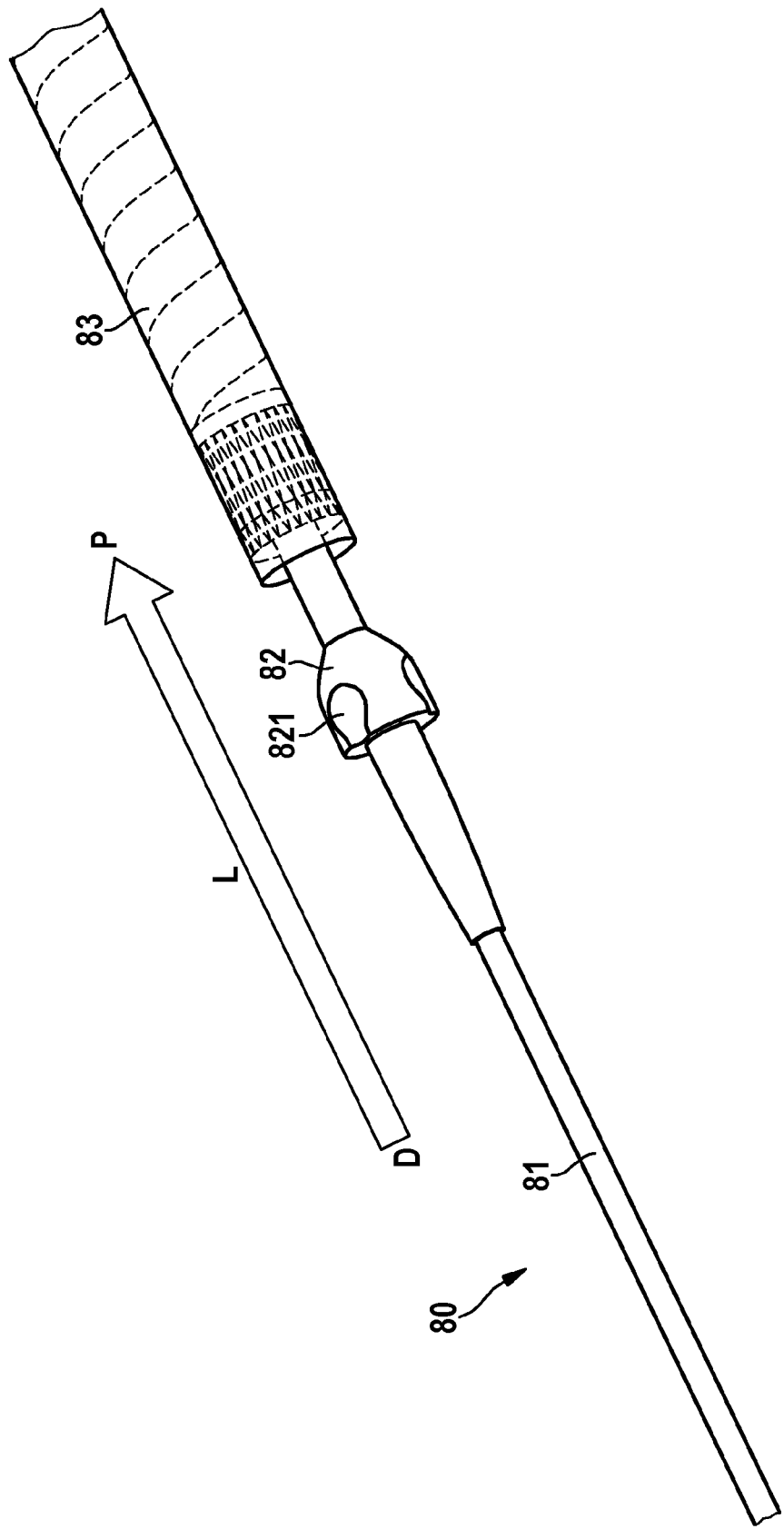
FIG. 3 is a partial illustration of a delivery device showing a portion of the shaft, the retaining member with recesses and a portion of the distal sheath in a partially retracted configuration.

FIG. 3 illustrates part of a delivery device 80. The delivery device is a catheter with an outer sheath 83, a shaft 81, a retaining member 82 attached to the shaft 81, and a handle 90. The retaining member 82 includes recesses 821 of a size that is adapted to receive the eyelets 74 of the prosthetic device 70. The delivery device 80 defines a compartment between the retaining member 82, an end of the shaft 81, which can for example be defined as a nose cone 84 (not shown in this figure), and the sheath 83.

FIG. 4A-R illustrates different steps of the method for loading the prosthetic device 70 into a compartment of the delivery device 80.

Figure 4C:
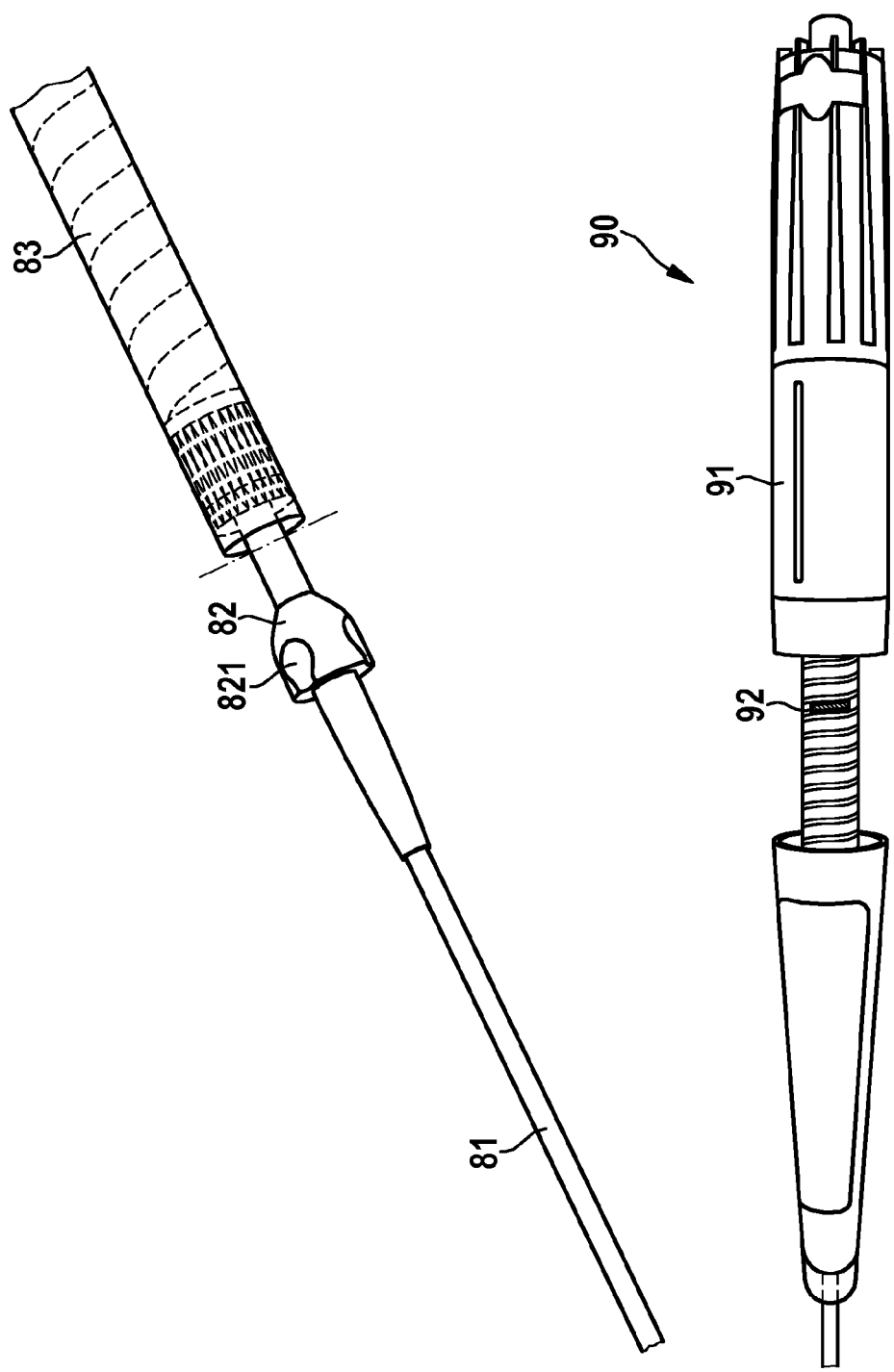
FIGS. 4A-R represent some of the steps of the loading method according to the invention.

In the step illustrated in FIG. 4A, the constriction member 40 is slid over the distal end of the delivery device 80 along the axis L in the proximal direction. The relative movement of the constriction member 40 to the delivery device 80 is indicated by an arrow. As a result of this step, at least a part of the delivery device 80 lies within the tubular constriction region 42 of the constriction member 40. FIG. 4B illustrates a step in which the compartment of the loading device 80 is opened by sliding the end of the sheath 83 proximally to expose at least part of the shaft 81. The movement of the sheath 83 relative to the shaft 81 is indicated by an arrow. The figure also shows the handle 90 of the delivery device. The handle is connected to the shaft 81 and the sheath 83 (not shown). The distal movement of the sheath 83 relative to the shaft 81 is in this case caused by a rotating the actuator 91 relative to the handle 90. FIG. 4C indicates the extent to which the sheath 83 is retracted in the proximal direction relative to the shaft. The distal end of the sheath 83 is indicated by a dotted line. The retraction of the sheath 83 by rotating the actuating element 91 on the handle 90 proximally beyond the mark 92 relative to the shaft 81 exposes the retaining element 82 with its recesses 821.

Figure 4D:
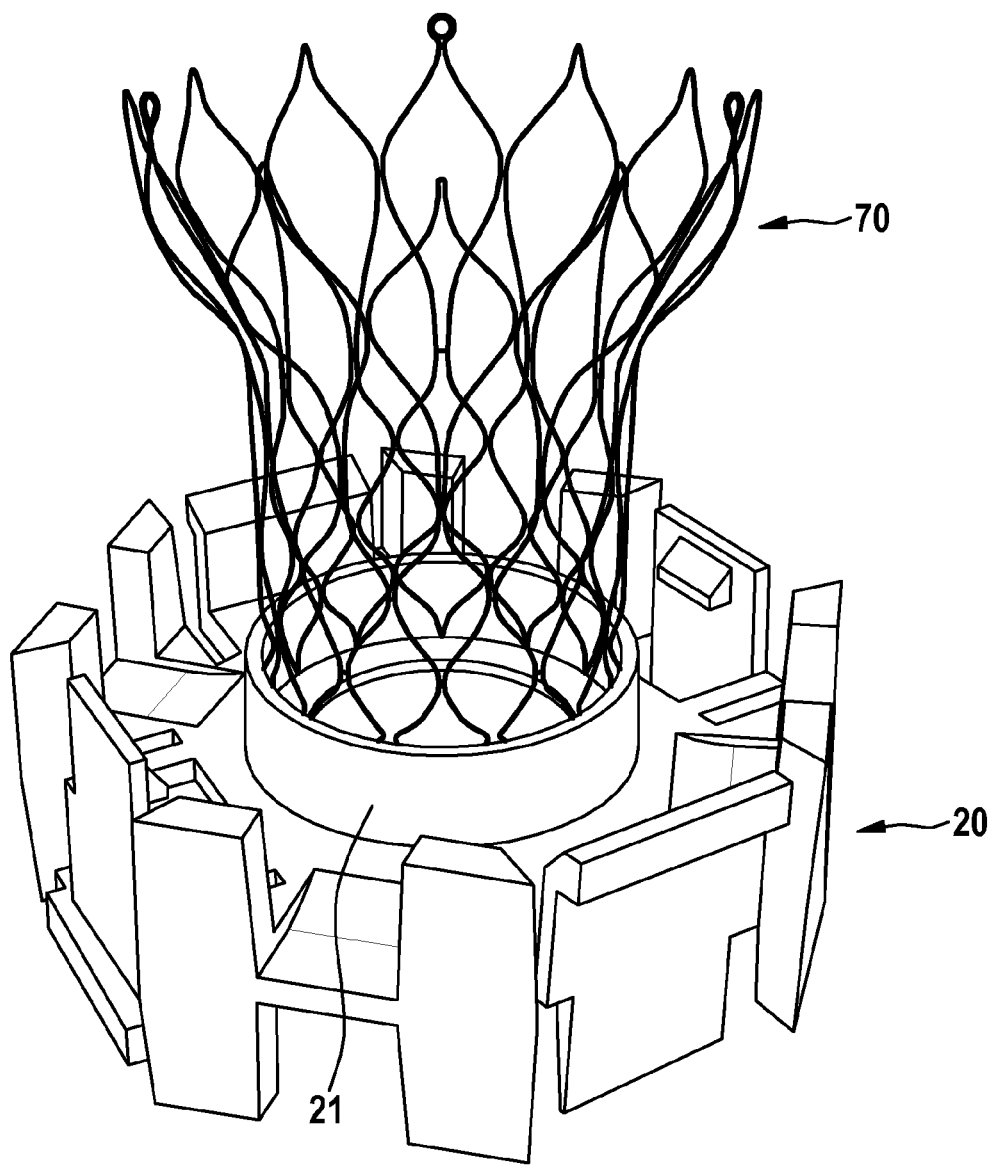
Figure 4E:
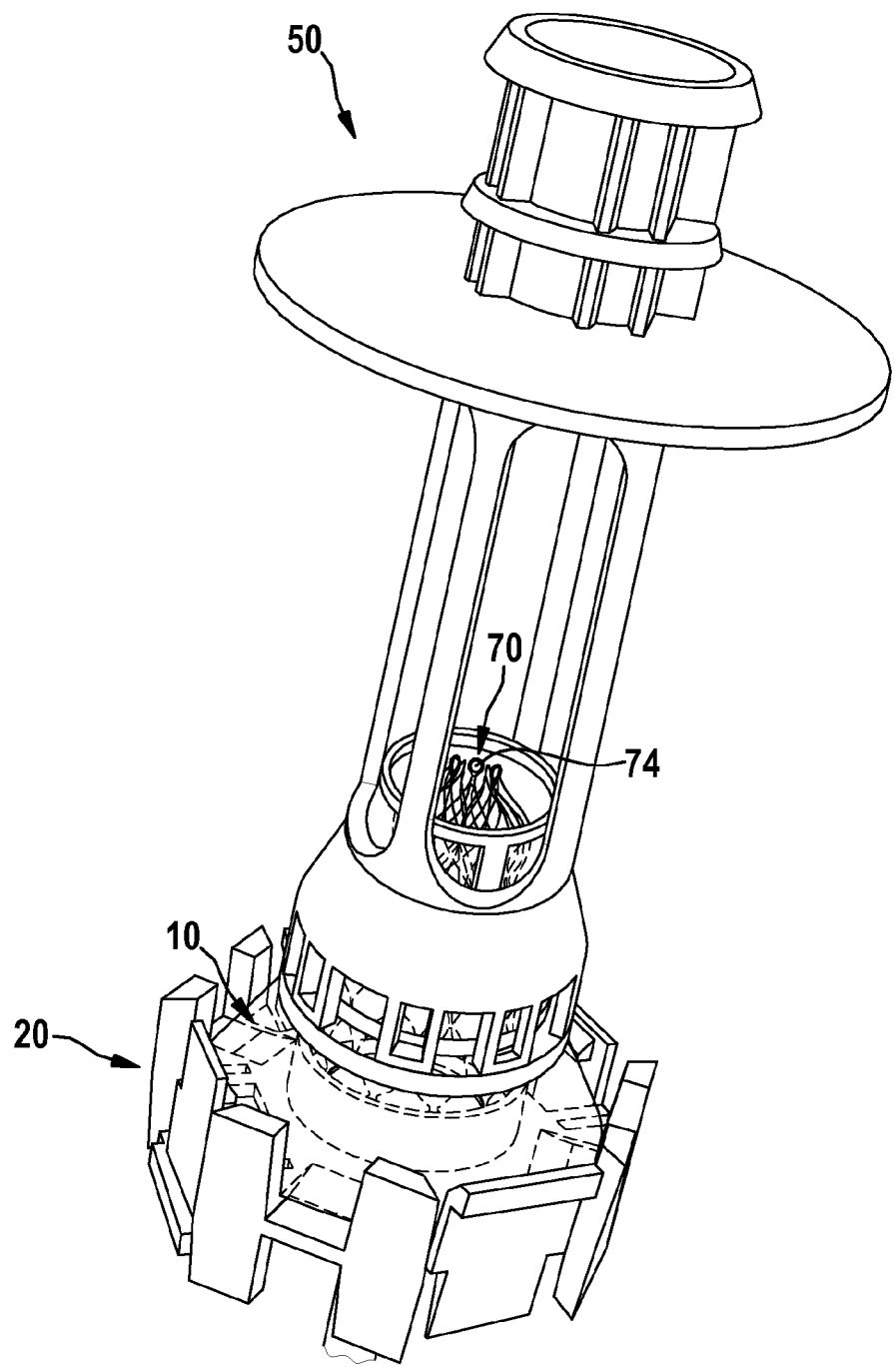

FIG. 4D illustrates the prosthetic device 70 loaded onto the support member 20. The proximal end of the prosthetic device 70 rests on one side of the support member 20, in the receptacle 21 that is configured as a collar. FIG. 4E illustrates the result of the step in which the support member 20 and the compression member 10 are releasably attached to each other to compress the distal end of the prosthetic device 70. The prosthetic device 70 is located inside the chamber of the compression member 10. The retainers 74 of the prosthetic device 70 are located in close proximity to each other in this configuration and protrude from an opening on the proximal side of the compression member 10. The figure also shows the spacer element 50, which is attached to the compression member 10.

Figure 4F:
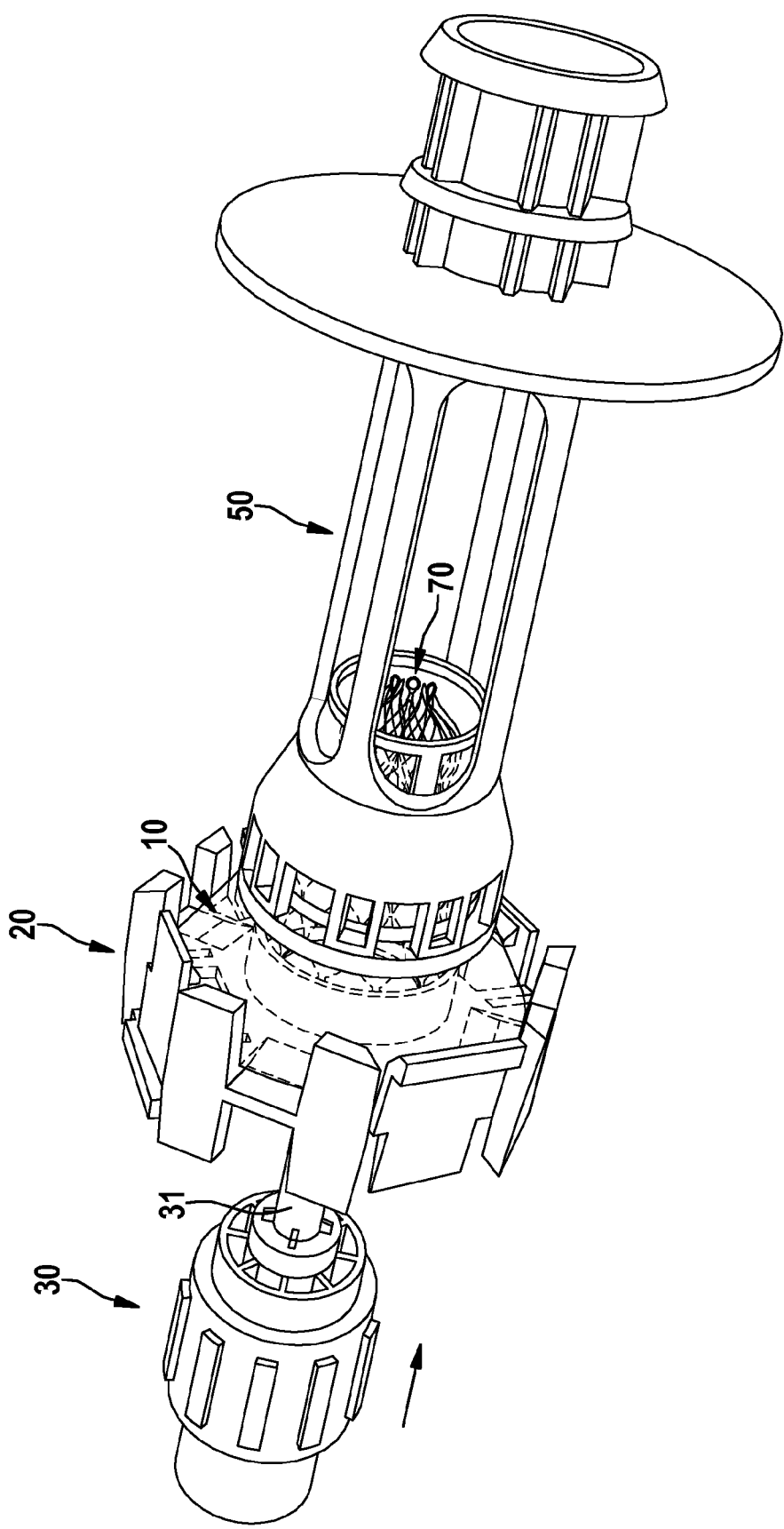
Figure 4G:
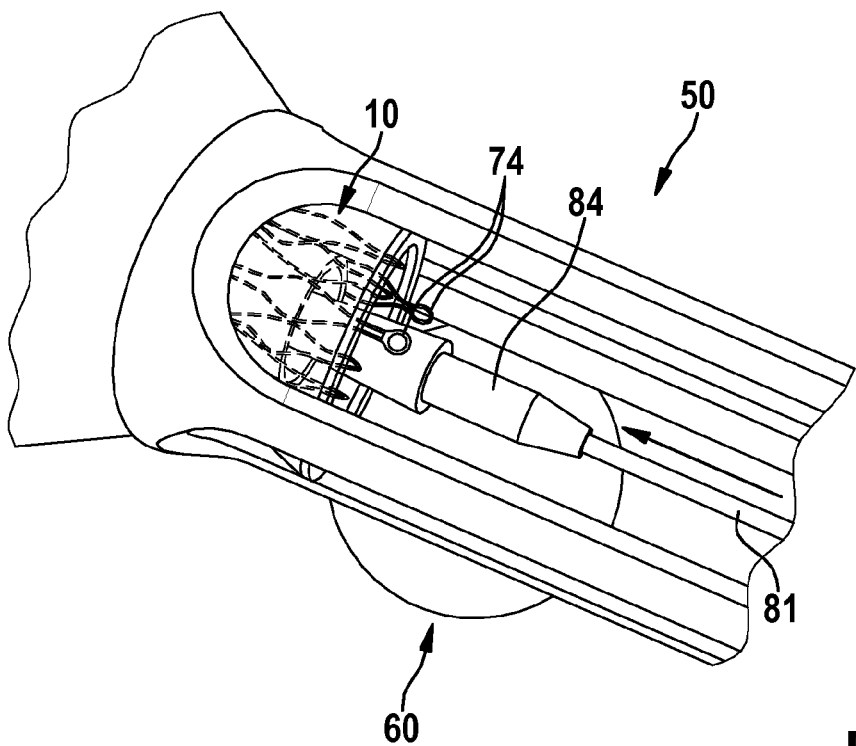
Figure 4H:
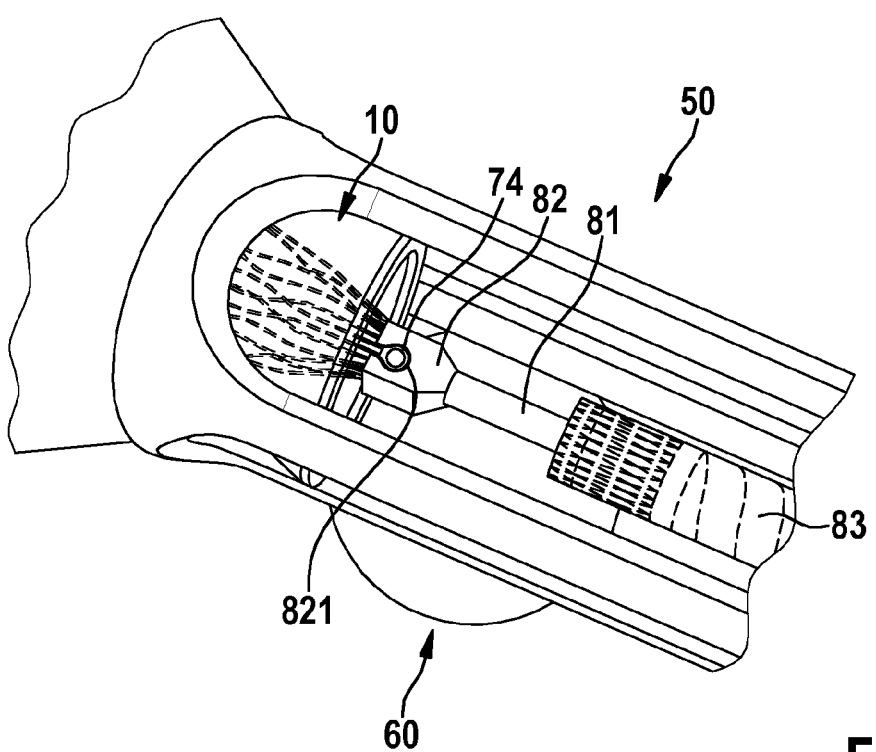
Figure 4I:
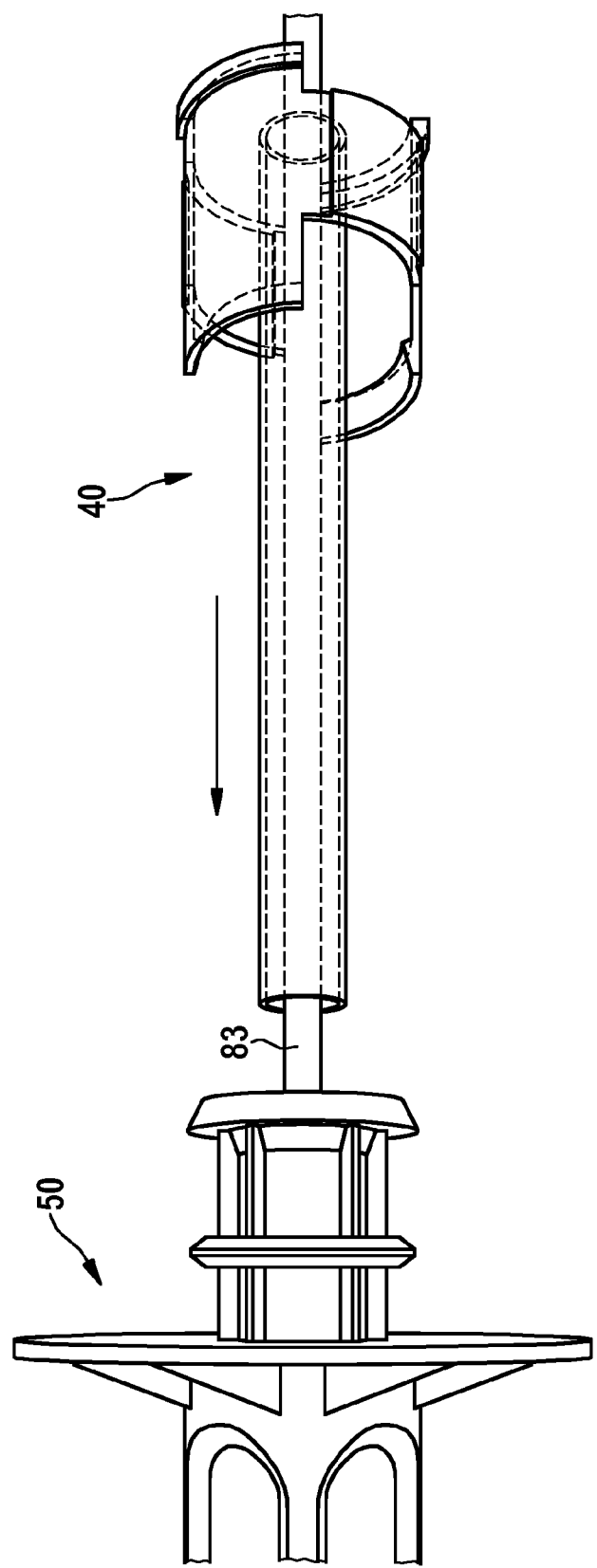

FIGS. 4F and 4G illustrate a splaying step in which the retainers 74 of the prosthetic device 70 are pushed apart in the radial direction in order to allow interaction with the retaining element 82 of the delivery device 80. This step is performed by inserting the hollow member 31 of the splay member 30 through the bore of the support member 20 and into the lumen of the prosthetic device 70 that is locked inside the compression member 10. The movement of the splay member 30 relative to the other parts of the loading device 100 and the prosthetic device 70 is indicated by an arrow in FIG. 4F. The effect of the interaction between the hollow member 31 of the splay member 30 and the lumen of the prosthetic device 70 is that the retainers 74 of the prosthetic device 70 are pushed apart in the radial direction. This leads to the opening of a gap between the retainers 74 through which the distal tip 84 of the shaft 81 of the delivery device 80 is inserted (see arrow in FIG. 4G). As shown in FIG. 4H, the delivery device 80 is inserted in the distal direction up to the point at which the retainers 74 of the prosthetic device 70 and the retaining member 82, and more particularly the recesses 821, coincide with each other along the longitudinal axis L. If necessary, the retainers 74 and the recesses 821 are also aligned with each other along the rotational axis by rotating the prosthetic device 70 around the longitudinal axis L. This can for example be done by rotating the support member 20, which causes the compression member 10 to rotate through their releasable attachment structures and in turn also causes the prosthetic device 70 to rotate. This step can be assisted through the use of the reflecting member 60, which allows the operator to monitor the alignment of retainers 74 and recesses 821 which would not be visible to the operator without the presence of the reflecting member 60. Once the retainers 74 and the recesses 821 are aligned with each other along the longitudinal axis L and rotationally, the hollow member 31 of the splay member 30 is moved distally along the axis L. This has the effect that the retainers 74 of the prosthetic device 70 move towards each other up to the point at which they interact with the recesses 821 of the retaining member 82 of the delivery device 80.

Figure 4J:
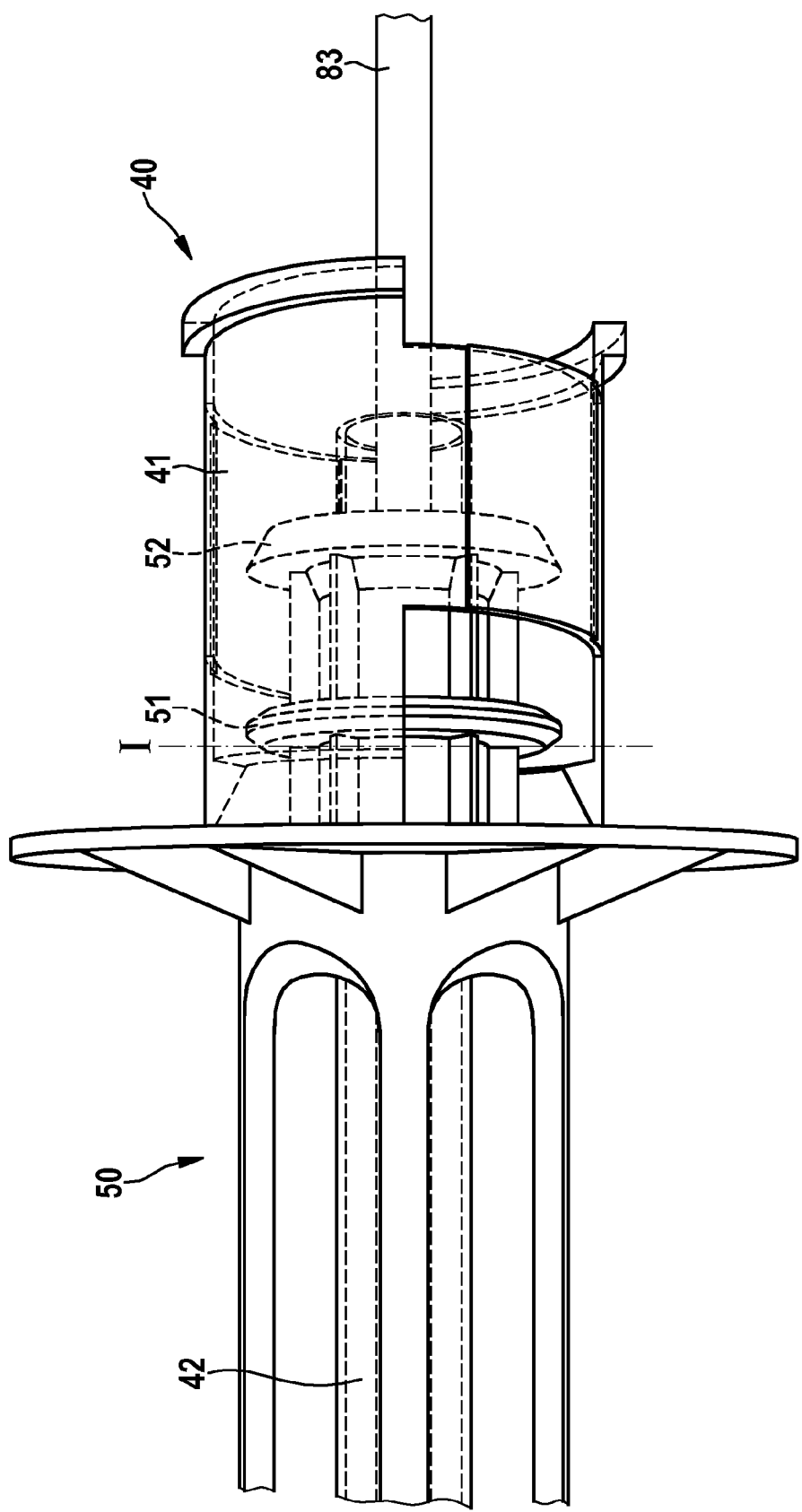
Figure 4L:
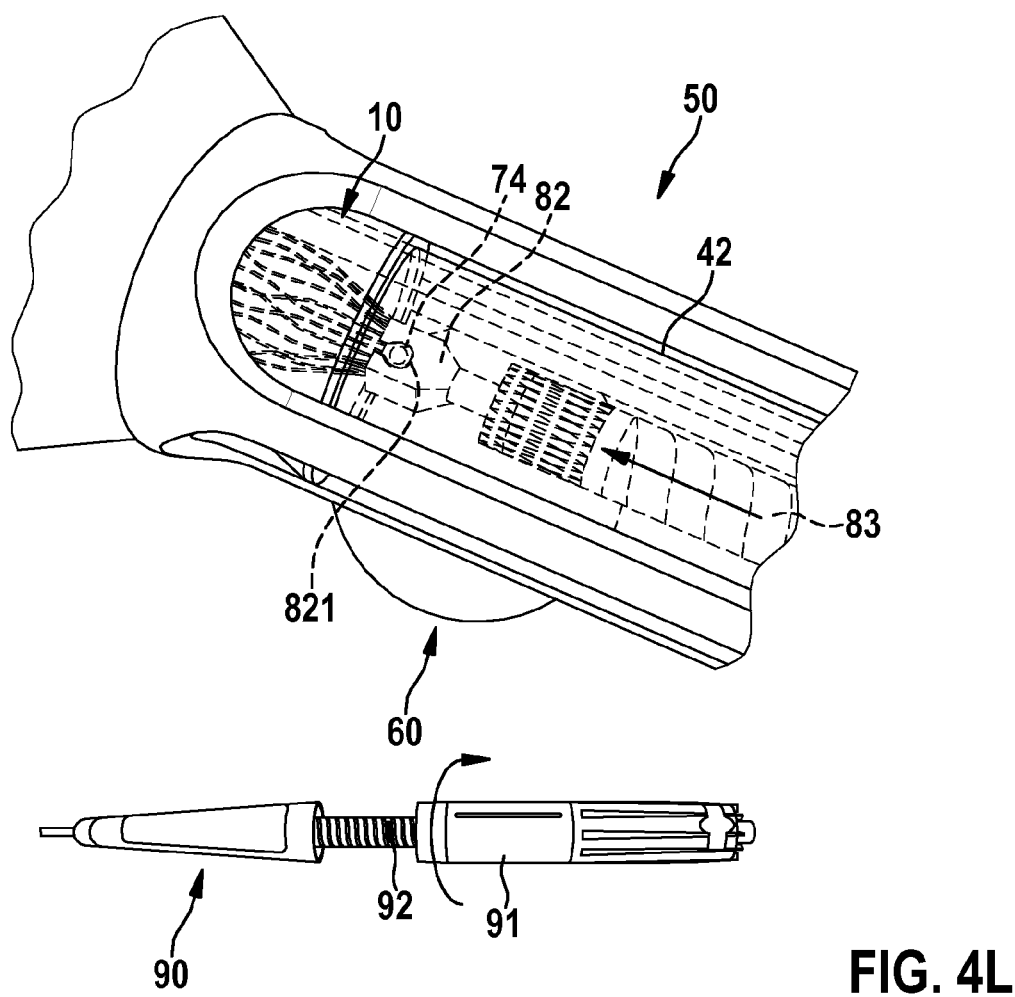

FIGS. 4I to 4L illustrate the step in which the constriction member 40 is slid distally along the longitudinal axis L into a first position in which the releasable attachment structures 51 and 41 of the spacer element 50 and the constriction member 40 interact with each other to provide the first locking position (indicated by the dotted lines I in FIG. 4J and 4K). In this position, the distal end of the tubular constriction region 42 of the constriction member 40 extends distally beyond the proximal end of the tapered chamber of the compression member 10. The distal end of the prosthetic device 70 is therefore radially compressed, as shown in FIG. 4K. This configuration is ideal for the sheath 83 of the delivery device 80 to be advanced distally to cover the recesses 821 of the retaining member 82 and the retainers 74 as shown in FIG. 4L (the arrow indicates the movement of the sheath 83 relative to the loading device 100 and the prosthetic device 70). The distal end of the prosthetic device 70 is indeed compressed in such a way that damage to the distal end of the sheath 83 is avoided. Damage to the distal end of the sheath 83 and optimal engagement with the prosthetic device 70 are further avoided by the fact that in this position, the distal ends of the prosthesis without retainers (the ends 77) are also further compressed towards each other in this first position. This ensures that the distal ends 77 can also be captured when advancing the sheath 83 in the distal direction since the combined radius of a circle formed by the ends 77 is smaller by Y than the radius of the sheath 83. The sheath 83 is in this case advanced distally by rotating the actuator 91 (which is attached to the sheath 83, this is not visible in the figure) relative to the handle 90. The position of the actuator 91 is thus shifted by the operator relative to the handle 90 up to a predefined marking 92 on the handle. The predefined marking 92 indicates when the position of the sheath 83 is such that the recesses 821 of the retaining member 82 are coved by the sheath 83. This is the position in which the prosthetic device is releasably attached to the delivery device through the interaction between the sheath 83, the recesses 821 of the retaining member 82 and the retainers 74.

Figure 4M:
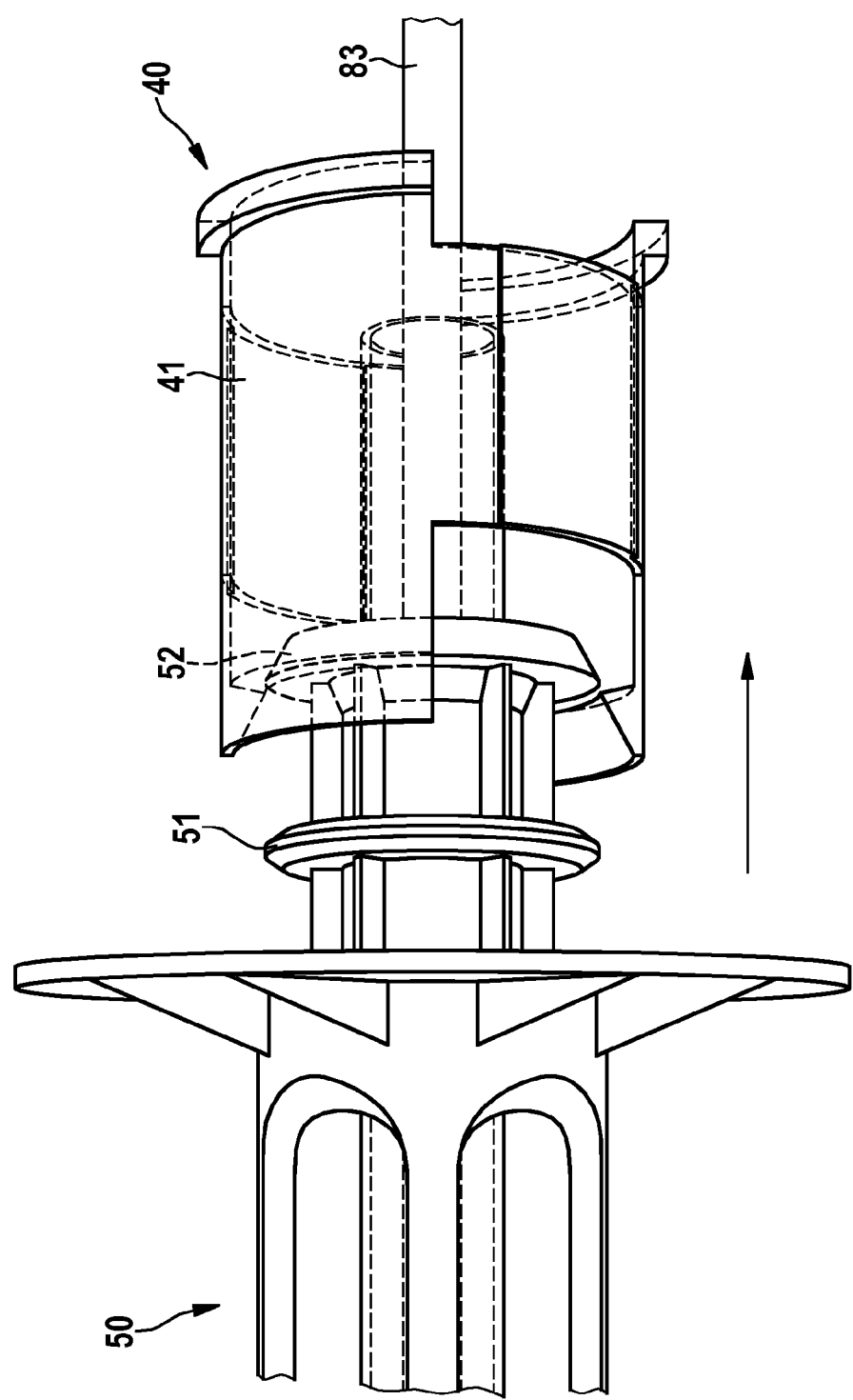
Figure 40:
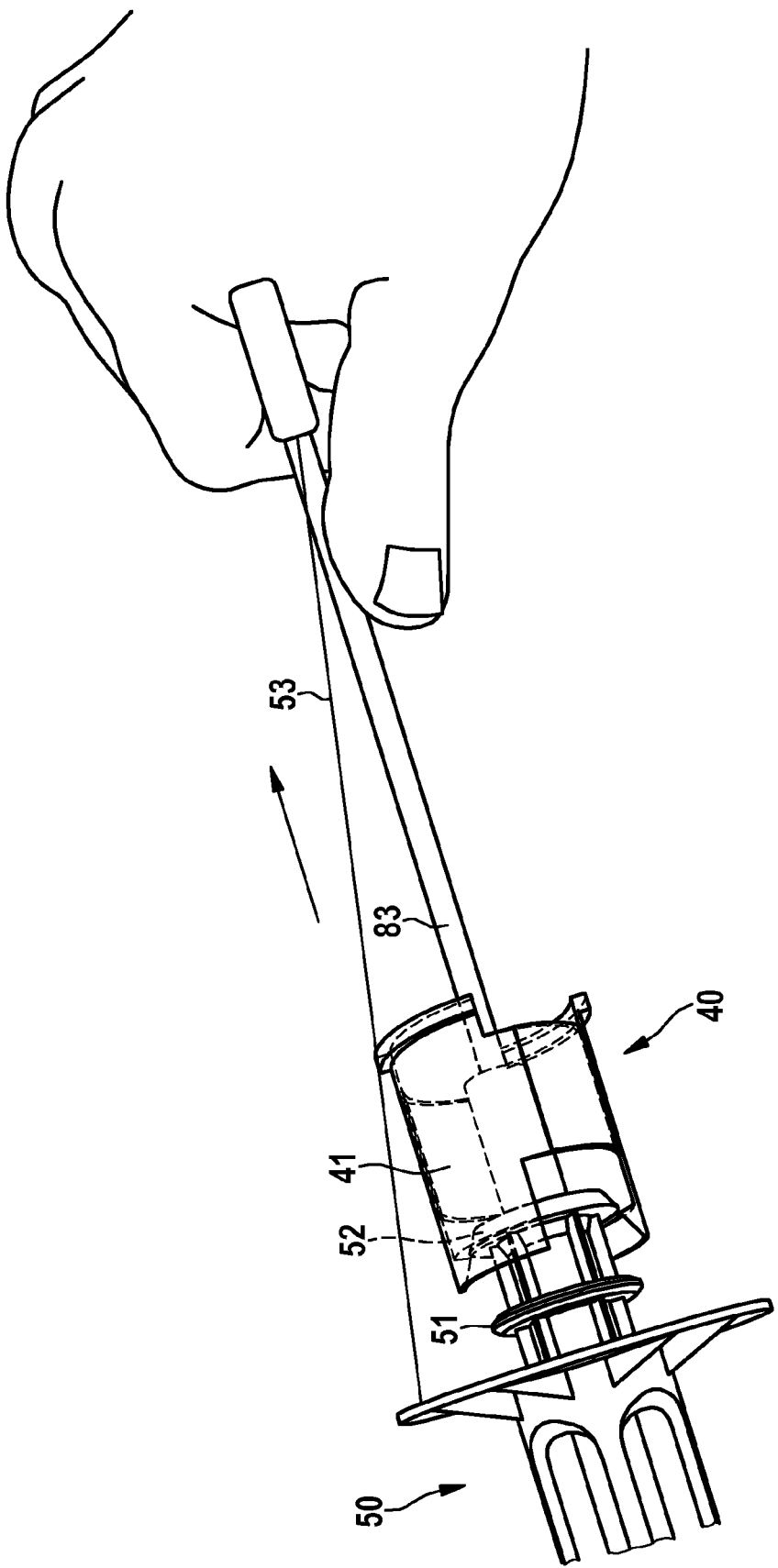

Once the prosthetic device 70 is releasably attached to the delivery device as shown in FIG. 4L, the constriction member 40 is moved in the proximal direction relative to the compression member 10 as shown by the arrow in FIG. 4M, into the second releasable attachment position (position II in FIG. 4N) defined by the releasable locking structures 41 and 52. In this second position, the distal end of the tubular constriction region 42 coincides with the proximal end of the tapered inner chamber along the longitudinal axis L as shown in FIG. 4N. Alternatively, the distal end of the tubular constriction region 42 could be positioned proximally to the proximal end of the tapered inner chamber. This ensures that the prosthetic device does not get damaged in the step of pulling the prosthetic device 70 into the lumen of the tubular constriction region 42 shown in FIGS. 4O and 4P. The prosthetic device 70 is indeed not subject to a sharp angle represented by the distal end of the constriction member 40 as would be the case in the first position (position I) illustrated in FIG. 4K. The sharp angles are indicated by circles at the interface between the distal end of the constriction member 40 and the prosthetic device 70 in FIG. 4K.

Figure 4P:
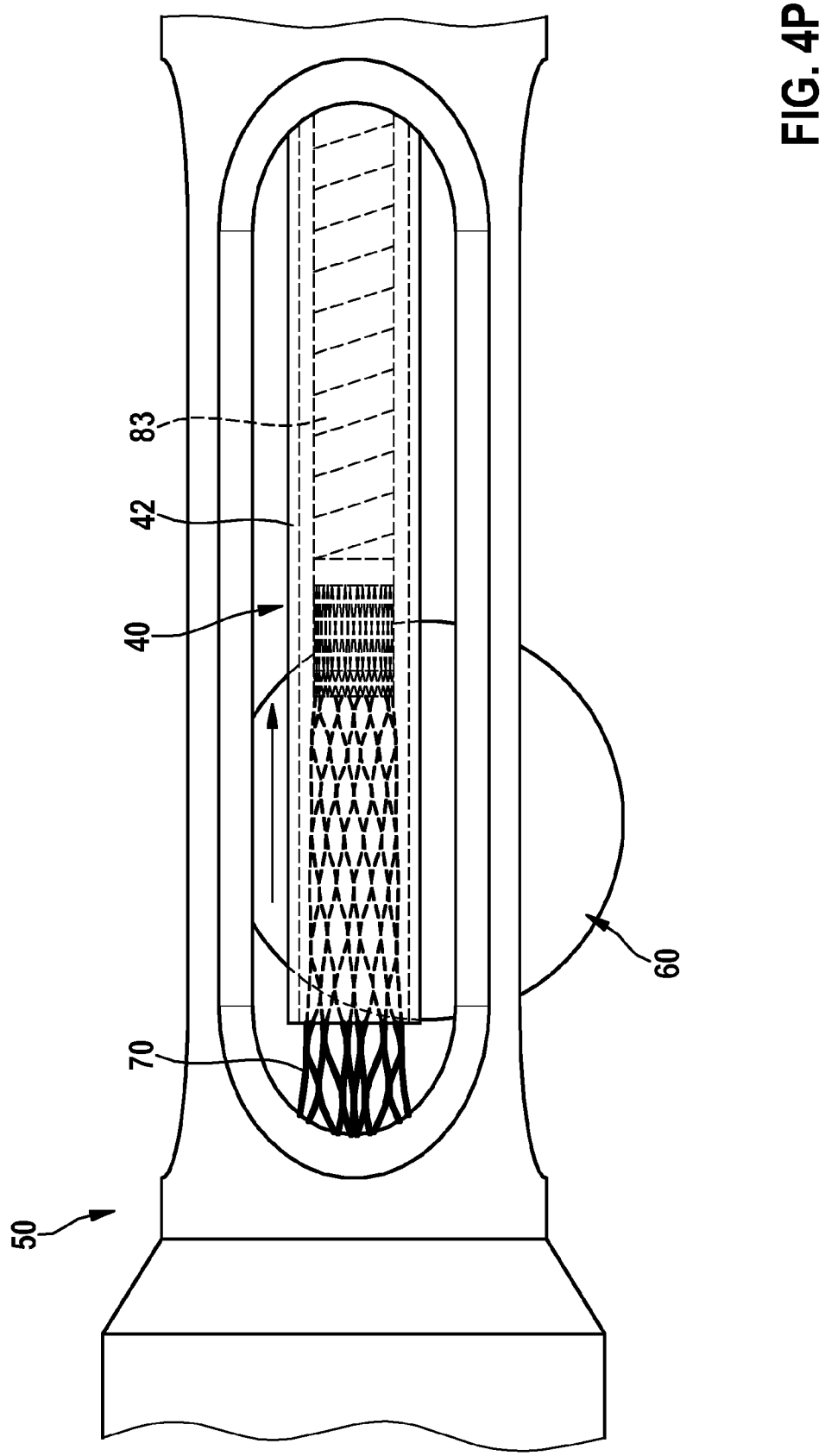

FIGS. 4O and 4P illustrate the step of pulling the prosthetic device 70 into the tubular constriction region 42 of the constriction member 40, and thereby reducing the diameter of the prosthetic device to fit inside the constriction region 42. This step can be performed, as indicated in FIG. 4O, by pulling the delivery device 80 in the proximal direction relative to the loading system 100 (the direction of the movement is indicated by the arrow in the figure). This is possible because at this point of the method, the prosthetic device 70 is releasably attached to the delivery device 80 as indicated in FIG. 4L and the description of that figure. The arrow in FIG. 4P shows the same movement of pulling the prosthetic device 70 into the tubular constriction region 42 and thereby reducing the diameter of the prosthetic device. FIG. 4O also shows how a stopper element with a handle 53 and a flexible element 54 can be used. In this case, the handle 53 of the stopper element is collocated with the shaft 83 of the delivery device at the proximal end of the constriction member 40 before pulling the delivery device 80 in the proximal direction. During the pulling movement of the delivery device 80 in the proximal direction relative to the loading device 100, the flexible portion 54 of the stopper element is tensed. When the flexible portion 54 is tensed, as indicated in FIG. 4O, the delivery device 80 has been pulled sufficiently in the proximal direction relative to the loading device 100 and the prosthetic device 70 rests in the tubular constriction region 42. The operator can proceed with the next step of the method without having to visually inspect the constriction member 40 or the prosthetic device 70.

Once the prosthetic device 70 rests in the tubular constriction region 42, the sheath 83 of the delivery device is moved distally relative to the shaft 81 and the prosthetic device 70 as indicated by the arrow in FIG. 4Q. This movement can be performed by further rotating the actuator 91 relative to the handle 90 of the delivery device 80. In this step, the compartment of the delivery device 80, which now includes the compressed prosthetic device 70, is closed. FIG. 4R shows the distal end of the delivery device 80 with the prosthetic device 70 enclosed within its compartment at the end of the loading procedure, once it has been removed from the loading system 100. The prosthetic device 70 can now be introduced into the human body and delivered to the location where it is to carry out its function.

FIG. 5 schematically shows the step that allows obtaining the configuration depicted in FIG. 4E. Only the tapered chamber of the compression member 10 and the prosthetic device 70 are schematically shown. The arrow indicates the relative movement of the compression member 10 and the prosthetic device 70 in this step. FIG. 5 also indicates the first and second diameters (d1, d2) of the ends of the tapered chamber of the compression member 10.

FIG. 6 schematically illustrates the step also depicted in FIG. 4G. Only the tapered chamber of the compression member 10, the prosthetic device 70 inside the chamber of the compression member 10 and the distal end of the delivery device 80, without the sheath 83, are represented. In this step, the prosthetic device 70 is mostly located inside the tapered chamber of the compression member 40 in such a way that the retainers 74 of the prosthetic device 70 as well as the distal ends 77 of the prosthetic device 70 protrude from the proximal end of the compression member. The retainers 74 of the prosthetic device 70 are pushed apart in the radial direction in this state by a hollow member 31 of a splay member 30 (not shown) and the distal end of the delivery device 80 is advanced in the distal direction into the gap between the retainers 74 as indicated by the arrow.

The invention claimed is:

1. A loading system for loading a self-expanding prosthetic device into a delivery device, the loading system comprising:
   a compression member comprising a chamber with a tapered inner surface extending along a longitudinal axis from a first distal end having a first diameter to a second proximal end having a second diameter that is smaller than the first diameter;
   a support member configured to be releasably attached to the first distal end of the compression member;
   a splay member;
   a constriction member, wherein the second proximal end of the compression member has an opening that is sized to slidably receive a first distal end of the constriction member; wherein the compression member and the constriction member are configured to be releasably attachable to each other directly or through a spacer element; and
   releasable attachment structures between the compression member and the constriction member configured to provide a first and a second attachment position of the compression member and the constriction member relative to each other; wherein the first and the second attachment positions are offset relative to each other along the longitudinal axis of the loading system.

2. The loading system according to claim 1, wherein in the first attachment position, the distal end of the constriction member is positioned distally relative to the second end of the tapered inner surface of the compression member along the longitudinal axis, and wherein in the second attachment position, the distal end of the constriction member coincides with or is positioned proximally to the second end of the tapered inner surface of the constriction member along the longitudinal axis.

3. The loading system according to claim 1, wherein the support member comprises a receptacle in the shape of an annular collar configured to receive an end of a prosthetic device.

4. The loading system according to claim 1, wherein the support member comprises a receptacle in the shape of an annular collar configured to receive an end of a prosthetic device on each of two opposed sides, wherein the collars on each of the opposed sides are configured to receive an end of a prosthetic device of different sizes.

5. The loading system according to claim 1, wherein the compression member and/or the constriction member is at least partially made of a transparent material.

6. The loading system according to claim 1, wherein the loading system comprises a spacer element that extends proximally along the longitudinal axis relative to the compression member, wherein the spacer element comprises an opening proximally to the second opening of the compression member that is configured to slidably receive the distal end of the constriction member, wherein the opening in the spacer element is aligned on the longitudinal axis with the second opening of the compression member and the centre of the through bore of the support member when the support member is releasably attached to the compression member.

7. The loading system according to claim 1, wherein the loading system comprises a spacer element that extends proximally along the longitudinal axis relative to the compression member, wherein the spacer element is configured to be rotatable around its longitudinal axis relative to the compression member.

8. The loading system according to claim 1, wherein the loading system comprises a spacer element that extends proximally along the longitudinal axis relative to the compression member, wherein at least a portion of the spacer element comprises at least one flat surface in its radially outermost circumference relative to the longitudinal axis.

9. The loading system according to claim 1, wherein the splay member comprises a hollow member.

10. The loading system according to claim 1, wherein the hollow member has an outer diameter sized to interact with an inner surface of the prosthetic device when the prosthetic device is located inside the tapered chamber of the compression member to reversibly push retainers located at the distal end of the prosthetic device away from each other in a radial direction relative to the longitudinal axis.

11. The loading system according to claim 10, wherein the splay member further comprises a retainer member and a biasing element located between the hollow member and the retainer member, wherein the retainer member comprises a surface that is adapted to rest on the distal side of the loading base and the biasing element is placed to bias the hollow member distally along the longitudinal axis relative to the retainer member.

12. The loading system according to claim 1, wherein the loading system further comprises a reflecting member placed so as to be adapted to allow monitoring of the loading of the prosthetic device into a delivery device from a position that would not otherwise be visible to the operator performing the loading procedure.

13. The loading system according to claim 1, wherein the constriction member has a lumen with an inner diameter that is configured to receive the prosthetic device in a compressed state.

14. A method for loading a self-expandable prosthetic device into a delivery device with a loading system according to claim 1, the method comprising:
 providing a delivery device comprising a shaft with a distal end, a retaining element attached to the shaft, a compartment adapted to receive the prosthetic device defined between a distal end of the shaft and the retaining element, and a distal sheath movable between a closed position fully covering the compartment and an open position uncovering the compartment, the prosthetic device comprising a stent and at least two retainers at its distal end and having an expanded and a collapsed condition;
 engaging the constriction member with the distal end of the delivery device;
 moving the distal sheath of the delivery device proximally to expose the retaining element;
 placing the proximal end of the prosthetic device on the support member and the compression member on the support member to enclose the prosthetic device within the tapered chamber of the compression member and thereby compressing the distal end of the prosthetic device;
 pushing the retainers of the prosthetic device contained in the compression member apart in the radial direction with a hollow member of the splay member;
 inserting the distal end of the shaft of the delivery device through the second opening of the compression chamber and through the lumen of the prosthetic device to align the retainers of the prosthetic device and the retaining element of the delivery device;
 withdrawing the hollow member in the distal direction so that the retainers of the prosthetic device engage with the retaining element of the delivery device;
 sliding the constriction member distally into the first attachment position;
 sliding the distal sheath of the delivery device distally to cover the retaining element;
 sliding the constriction member proximally into the second attachment position;
 pulling the prosthetic device into the constriction member;
 closing the compartment of the delivery device by sliding the distal sheath distally into the closed position.

15. The method according to claim 14, wherein the part of the loading system that comprises the prosthetic device is placed at a temperature of between 0° C. and 15° C., preferably 2° C. to 8° C., at least during the step of pulling the prosthetic device into the constriction member.

16. A loading system for loading a self-expanding prosthetic device into a delivery device, the loading system comprising:
 a compression member comprising a chamber with a tapered inner surface extending along a longitudinal axis from a first distal end having a first diameter to a second proximal end having a second diameter that is smaller than the first diameter;
 a support member configured to be releasably attached to the first distal end of the compression member;
 a splay member;
 a constriction member, wherein the second proximal end of the compression member has an opening that is sized to slidably receive a first distal end of the constriction member; wherein the compression member and the constriction member are configured to be releasably attachable to each other through a spacer element, wherein the spacer element extends proximally along the longitudinal axis relative to the compression member; and
 releasable attachment structures between the compression member and the constriction member configured to provide a first and a second attachment position of the compression member and the constriction member relative to each other; wherein the first and the second attachment positions are offset relative to each other along the longitudinal axis of the loading system.

* * * * *